United States Patent
Lvovich et al.

(10) Patent No.: US 6,861,851 B2
(45) Date of Patent: Mar. 1, 2005

(54) METHOD FOR ON-LINE MONITORING OF QUALITY AND CONDITION OF NON-AQUEOUS FLUIDS

(75) Inventors: Vadim F. Lvovich, Cleveland Heights, OH (US); David B. Skursha, Mentor, OH (US); Frederick P. Boyle, Kirtland, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 10/271,885

(22) Filed: Oct. 16, 2002

(65) Prior Publication Data

US 2004/0075448 A1 Apr. 22, 2004

(51) Int. Cl.[7] .............................................. G01R 27/08
(52) U.S. Cl. ....................... 324/698; 324/553
(58) Field of Search ............................. 73/10; 324/698, 324/704, 707, 553; 340/663

(56) References Cited

U.S. PATENT DOCUMENTS

| | | | |
|---|---|---|---|
| 5,331,287 A | 7/1994 | Yamagishi et al. | 324/724 |
| 5,518,590 A | 5/1996 | Fang | 205/780.5 |
| 5,540,086 A | 7/1996 | Park et al. | 73/53.05 |
| 5,656,767 A | 8/1997 | Garvey, III et al. | 73/61.44 |
| 5,824,889 A | 10/1998 | Park et al. | 73/116 |
| 5,889,200 A | 3/1999 | Centers et al. | 73/53.01 |
| 5,933,016 A | 8/1999 | Kauffman et al. | 324/698 |
| 6,028,433 A | 2/2000 | Cheiky-Zelina et al. | 324/663 |
| 6,217,745 B1 | 4/2001 | Fang | 205/775 |
| 6,268,737 B1 * | 7/2001 | Marszalek | 324/663 |
| 6,278,281 B1 * | 8/2001 | Bauer et al. | 324/441 |
| 6,380,746 B1 * | 4/2002 | Polczynski et al. | 324/446 |
| 6,443,006 B1 * | 9/2002 | Degrave | 73/304 C |
| 2002/0125899 A1 * | 9/2002 | Lvovich et al. | 324/698 |

FOREIGN PATENT DOCUMENTS

| | | |
|---|---|---|
| DE | 10121186 A1 | 11/2001 |
| EP | 0531585 A1 | 3/1993 |
| EP | 1014082 A2 | 6/2000 |
| JP | 406082408 | 3/1994 |
| WO | WO 91/09922 | 7/1991 |
| WO | WO 03/054482 A2 | 7/2003 |

OTHER PUBLICATIONS

Derwent Abstract of DE 10121186, Accession No. N2002–056281.

Electrical Conductivity Method for Evaluation of Oxidative Degradation of Oil Lubricants; Lubrication Engineering, vol. 48, 7, 539–544; 1991, by Atsushi Sato and Takashi Oshika.

(List continued on next page.)

*Primary Examiner*—Anjan Deb
*Assistant Examiner*—Walter Benson
(74) *Attorney, Agent, or Firm*—Teresan W. Gilbert; Michael F. Esposito

(57) ABSTRACT

A method for determining quality and condition of a highly resistive fluid in transportation and industrial equipment. The method uses apparatus that applies a multitude of oscillating voltage signals at determined frequencies and offsets to electrodes immersed in the fluid and quantifies fluid response to the signals. The method monitors response of the fluid to a preferred three fixed electrical signals applied by the apparatus, a high and a medium frequency signal with zero offset voltage and a low frequency signal with an offset voltage. For apparatus or applications where the monitored fluid is not controlled to constant temperature, the method includes correcting the temperature sensitive fluid responses for temperature variations for the fluid quality and condition determination. The method can also include determining when essentially complete fluid exchanges are made to the equipment without need for additional input.

16 Claims, 9 Drawing Sheets

OTHER PUBLICATIONS

Development of an On–Board Type Oil Deterioration Sensor; SAE Technical Paper Series, Oct., 1993.

Proceedings of the Symposium on Chemical Sensors; The Electrochemical Society, Inc.. Proceedings vol. 87–9; Turner.

In–Situ Oil Condition Monitoring in Passenger Cars; Lubrication Engineering, vol. 50, 8, 605–611: Lee et al.

Development of an Automatic Engine Oil–Change Indicator System; SAE Technical Paper Series; Schwartz et al.; Feb. 23–27, 1987.

A Capacitive Oil Deterioration Sensor; Saloka et al.

Oil Maintenance Tester: A New Device to Detect the Degradation Level of Oils; Lubrication Engineering; Nov. 1986; Kato et al.

In Situ Electrochemical Sensor for Measurement in Nonconductive Liquids; J. Electrochemical Society, vol. 140, No. 3, Mar. 1993; Joseph et al.

The development of in situ electrochemical oil–conduction sensors; Sensors and Actuators B, 17 (1994) 179–185; Wang et al.

In situ monitoring of high–temperature degraded engine oil condition with microsensors; Sensors and Actuators B, 20 (1994) 49–54; Lee et al.

The application of a.c. impedance technique for detecting glycol contamination in engine oil: Sensors and Actuators B 40 (1997) 193–197; Want et al.

"Smart Sensing" of Oil Degradation and Oil Level Measurements in Gasoline Engines; SAE Technical Paper Series; Mar. 6–9, 2000, Basu et al.

Development of an On–Board Type Oil Deterioration Sensor; SAE Technical Paper Series; Oct. 18–21, 1993; Morishita et al.

Low Cost Oil Deterioration Sensor for On–Board Diagnostics; Park et al.

Corresponding PCT International Publication No. WO2004/036210 A1 published Apr. 29, 2004 and Search Report.

* cited by examiner

METHOD FOR ON-LINE MONITORING OF QUALITY AND CONDITION OF NON-AQUEOUS FLUIDS

BACKGROUND OF THE INVENTION

The present invention relates to a method for monitoring the quality and the condition of a highly resistive fluid(s) while in use in transportation or industrial equipment including but not limited to vehicles, machines, devices and the like. In particular, the invention relates to a cost-effective method for on-line analysis of a fluid's electrochemical impedance resulting in the diagnoses of the initial fluid quality and of changes of the fluid condition, for examples chemical changes, depletion of performance additives, contamination with unwanted liquids or solids and the like. The present invention is of particular value for monitoring the quality and conditions of hydrocarbon-based fluids.

Fluids are a critical component for the proper operation of many types of equipment. For example, lubricants are needed for an internal combustion engine to efficiently provide power over a long service life; quality fuel is needed for proper engine operation with minimal emissions; and metal working fluid is needed in machining equipment for rapid metal removal and maximum tool life. For optimum performance, a fluid must initially be of the proper quality for the application, that is, the fluid must have an appropriate base fluid and proper performance additives, such as dispersants and detergents. Also for optimum equipment performance, fluid condition must remain within determined limits. While most device owners and process operators depend on suppliers to provide proper quality fluids and regular fluid additions and exchanges to maintain proper fluid condition, these dependencies do not protect against accidental fluid substitutions, or catastrophic fluid failure. In addition, owners or operators may be able to reduce operation cost if fluid maintenance were to occur only when needed based on monitored fluid condition.

There is a need for on-line fluid monitoring that allows essentially "real-time" determination of a fluid's initial quality and continuing condition while in use. Achieving appropriate fluid monitoring method and apparatus, however, has been quite difficult for many applications for a variety of reasons. Most transportation and industrial fluids are complex mixtures of base fluids and additives, which even without contaminants do not lend themselves to easy analysis. Most fluids are used or consumed in a relatively harsh environment, which is not suited for typical analytical equipment and methods. Also there are severe cost constraints, both initial and long term, for any method and apparatus.

Lvovich, et al., U.S. Ser. No. 09/803,299 entitled "Method and Apparatus for On-Line Monitoring of Quality and/or Condition of Highly Resisting Fluids" discloses a means for determining information about highly resistive fluids. In particular, by applying a multitude of AC electrical signals of unique frequency and offset voltage to a fluid, measuring the fluid's electrical response at each applied signal, and analyzing the responses to determine a fluid's quality and/or condition. The application, however, does not provide a detailed method of what signals to apply, which fluid properties to determine from the measured fluid's electrical response, and how to use those properties in an analysis that allows an efficient and effective determination of a fluid's quality and/or condition.

Accordingly, the present invention provides a method that includes the signals to apply, the fluid properties to determine from responses to the applied signals and the analysis of those fluid properties for essentially continuous, such as intermittent, continuous, repeatedly or combinations thereof, on-line determination of fluid quality and/or condition while in use in industrial or transportation applications.

SUMMARY OF THE INVENTION

The present invention relates to a method for monitoring the quality and condition of a highly resistive fluid, in particular, a hydrocarbon-based fluid used in transportation and industrial applications.

The invention comprises applying a high and a medium frequency, fixed-amplitude, zero-offset voltage signals and a low frequency, fix-amplitude non-zero-offset voltage signal between electrodes immersed in the monitored fluid and measuring the fluid-dependent response to the signals. Further, the invention in another embodiment comprises applying only the medium and low frequency signals between electrodes and measuring the fluid dependent responses for fluids in applications wherein changes in the fluid's high frequency response is substantially less significant than the changes in the fluid's medium and low frequency responses.

The method of the invention comprises comparing the magnitude and the rate-of-change of the measured fluid responses, relative to initial value for the high frequency response and peak values for the medium- and low-frequency responses, to thresholds to determine the quality and condition of the fluid.

One feature of the invention is that the frequency and offset voltage of each applied signal is predetermined as a function of apparatus electrode geometry, fluid temperature or temperature range, chemical composition of the fluid being monitored or combinations thereof.

Another feature of the invention is that the fluid responses is measured at fixed fluid temperature or at variable fluid temperature and converted or corrected to minimize the effect of temperature variation on fluid response using appropriate formulae or look-up tables.

Another feature of the invention is that formulae or look-up tables used to convert or correct fluid responses for temperature variations can be permanently fixed, or can be updated by appropriate means to allow for changes in formulation of fresh fluid, that is, unused fluid, added to the equipment.

Another feature of the invention is that formulae or look-up tables used to convert or correct fluid responses for temperature variations can be automatically updated each time the fluid temperature increases between two temperature thresholds at greater than a preset rate.

Another feature of the invention is that the thresholds can be predetermined, can be determined based on response comparisons to other thresholds, or can be up-dated by appropriate means to allow for changes in formulation of fresh fluid added to the equipment.

Another feature of the invention is that essentially complete fluid exchanges made to the equipment can be determined without need for additional input in order to reset the fluid condition and quality thresholds for the fresh fluid added to the equipment.

The present invention may be more readily apparent from the following figures.

DETAILED DESCRIPTION OF THE INVENTION

The invention relates to a method for on-line monitoring and/or detecting the quality and condition of a highly resistive fluid in industrial and transportation uses. The highly resistive fluid is a non-aqueous fluid, that is, not water based, and substantially water free. The non-aqueous fluid may, however, contain water contaminants.

Figure 1:
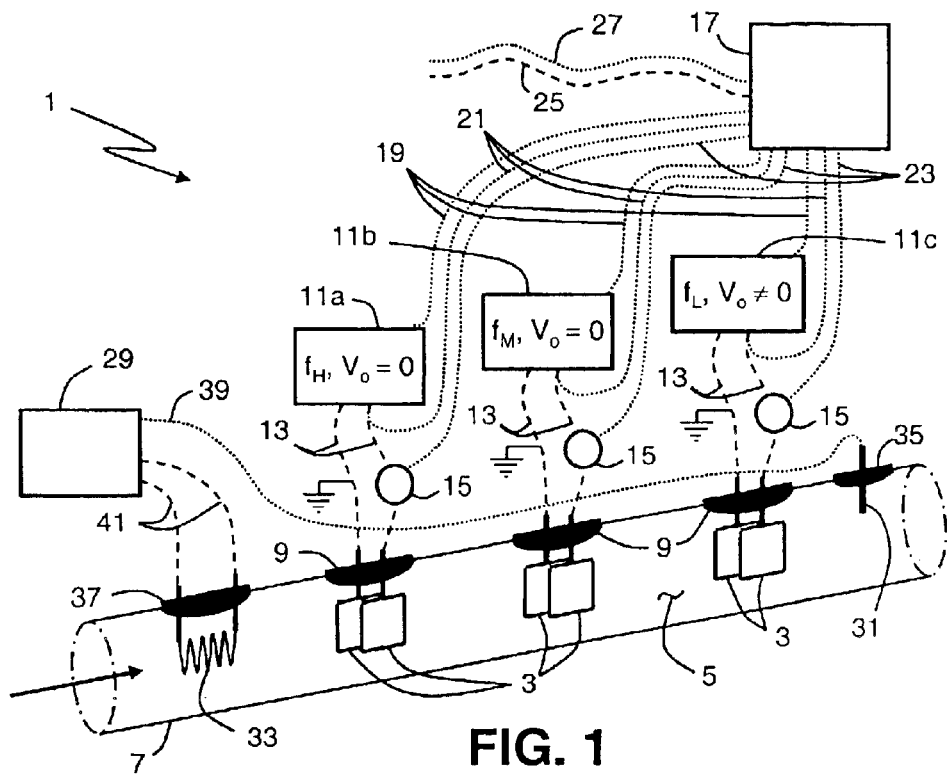
FIG. 1 is a schematic representation of an apparatus that can be used with the current invention, where the apparatus controls fluid temperature.

FIG. 1 is a schematic illustration of an apparatus 1 that can be used to collect appropriate data required for the monitoring and detecting of on-line the characterization of a fluid. Apparatus 1 includes three pairs of essentially parallel electrodes 3 immersed in highly resistive fluid 5, in conduit 7. The pairs of electrodes 3 are fixedly held in and electrically isolated from conduit 7, by mounts 9. Apparatus 1 also includes three signal generators 11a, 11b, 11c that supply sinusoidal signals of fixed amplitude, frequency and offset voltage through electrical conduits 13, to an associated pair of electrodes 3. As used herein, a signals offset voltage is defined as the time averaged voltage of the signal. The frequencies and offset voltages of signal generators 11a, 11b, 11c are preset based on the geometry of electrode pairs 3 (each electrode pair need not have the same geometry), and by type and temperature of fluid 5. Generator 11a, supplies a signal with frequency $f_H$ and zero offset-voltage, generator 11b, supplies a signal with frequency $f_M$ and zero offset-voltage, and generator 11c, supplies a signal with frequency $f_L$ and a non-zero offset-voltage, where $f_H > f_M > f_L$. One electrical conduit 13 of each signal generator 11a, 11b, 11c is grounded for a voltage reference and the other conduit 13 includes a current sensor 15, which measures electrical current flow through conduit 13. Apparatus 1 also includes controller 17 with electrical conduits 19 for powering each signal generator 13, electrical conduits 21 for monitoring output voltage of each signal generator 13, and electrical conduits 23 for monitoring current flow measured by each current sensor 15. Controller 17 also has electrical conduit 25 to receive power and electrical conduit 27 to communicate information either to or from the controller.

Apparatus 1 further includes a temperature controller 29, thermocouple 31, and heater 33. Thermocouple 31 and heater 33 are fixedly held in conduit 7 by mounts 35 and 37, respectively and electrically communicate with temperature controller 29 via electrical conduits 39 and 41, respectively, such that in operation controller 29 applies power to heater 33 through conduits 41 to maintain the temperature of the fluid flowing past the thermocouple 31 at a determined fixed temperature; thereby maintaining the fluid temperature at electrodes 3.

In operation, fluid 5 flows through conduit 7, in direction shown by arrow, and between pairs of electrodes 3, power is applied to controller 17 through electrical conduit 25, and temperature controller 29, monitors the temperature of fluid 5 with thermocouple 31 and electrical conduit 39 and applies appropriate power through conduits 41 to heater 33 to maintain the fluid in the conduit at a preset temperature. When used with a method of this invention, the method determines when controller 17 powers signal generators 11a, 11b, 11c to apply signal through conduits 13 and pairs of electrodes 3 to fluid 5. The electrical response of fluid 5 to the applied signals causes current to flow and to be measured by current sensors 15. Controller 17 monitors the applied signals and the corresponding current flows through electrical conduits 19, 21 respectively, and compares magnitude and phase of the voltage and current signals to calculate electrochemical impedance of fluid 5 at the three applied signals ($f_H, V_o=0$), ($f_M, V_o=0$) and ($f_L, V_o \neq 0$). A method of this invention uses the impedance data to determine quality and/or condition of fluid 5. Controller 17 can receive information used in the method of this invention through electrical conduit 27, for example, information that an essentially complete fluid exchange has occurred or information that is used in the determination of fluid quality and/or condition can be received. A method of this invention can communicate information about the fluid quality and/or condition determination from controller 17 through electrical conduit 27. The fluid quality and/or condition information can be immediately communicated to a signaling device, for example a warning light, to alert an equipment operator, to a central maintenance facility to notify maintenance personnel when fluid maintenance is needed, or to a device that can turn equipment using the fluid "off" to prevent damage. The fluid quality and/or condition information can be communicated from stored memory when queried by, for example, a service technician's diagnostics system.

While FIG. 1 shows apparatus 1 that monitors fluid response to three fixed applied signals of high, medium and low frequency, the present invention can, for fluids in applications where changes in the fluid's high-frequency response is substantially less significant than the changes in the fluid's medium- and low-frequency responses, use apparatus that monitors fluid response to two fixed applied signals of medium and low frequency. For a two-frequency embodiment an apparatus would not need signal generator 11a that applies signal ($f_H$,$V_o$=0), and electrodes 3, current sensor 15 and electrical conduits 13, 19, 21, 25 associated with signal generator 11a shown in FIG. 1.

While FIG. 1 shows electrodes 3 of apparatus 1 in conduit 7 with flowing fluid 5, apparatus 1 can be mounted in any location where fluid 5 flows between electrode pairs 3 in a manner that allows the fluid between the electrodes to be, at all times, maintained at a fixed temperature and representative of the current quality/condition of the fluid in the equipment being monitored. For example, apparatus 1 can be mounted in a fluid reservoir or sump where the heater 33 is located in close proximity and the motion of fluid 5 is sufficient to allow appropriate heating and relatively uniform mixing and exchange of fluid within the equipment.

While FIG. 1 shows three signal generators 11a, 11b, 11c and three pairs of electrodes 3, an apparatus embodiment can have a fewer number of generators and electrode pairs if a signal generator is capable of being controlled to apply one desired frequency and offset-voltage, for example, $f_H$,$V_o$=0, to fluid 5 and the response measure, for a first period of time followed by being controlled to apply another frequency and offset-voltage for a second period of time, and repeated for a third period of time and repeating that sequence such that the three signals ($f_H$,$V_o$=0), ($f_M$,$V_o$=0) and ($f_I$,$V_o$≠0), are applied and the fluid responses measured by the apparatus in a time efficient manner.

While FIG. 1 shows electrodes 3 to be flat rectangle with essentially only one surface of each electrode applying a signal from a signal generator to the fluid between the electrodes, an apparatus embodiment can have electrodes of other geometry, for example the electrodes can be concentric-cylinders or can be flat with a multitude of finger-like sections, and an apparatus embodiment can have electrodes with multiple surfaces or surface sections, which may or may not directly face surfaces or surfaces sections of the other electrode, for applying a signal to the fluid, for example interdigitated electrodes where finger-like sections of one electrode alternate with finger-like sections of the other electrode.

While FIG. 1 shows apparatus 1 to include temperature controller 29, a temperature controller may not needed if the temperature of fluid 5 is maintained at- or acceptably close to- a desired temperature by means external to the apparatus. For examples, if the equipment using fluid 5 operates in a steady-state manner that maintains the fluid temperature at a constant temperature, or if the fluid flows through a heat exchanger to either heat or cool the fluid to maintain a performance property, temperature controller 29, thermocouple 31 and heater 33 may not be needed.

While FIG. 1 shows apparatus 1 with no communication between temperature controller 29 and controller 17, an apparatus embodiment can have communication between the two controllers such that the method of this invention can use temperature information when determining fluid quality and condition or so that information about required fluid temperature can be communicated to the temperature controller.

While FIG. 1 shows apparatus 1 as individual components, the apparatus embodiment can integrate components and functions of the apparatus into a compact package, which, for example reduces cost, size and/or power requirement of the apparatus.

Figure 2:
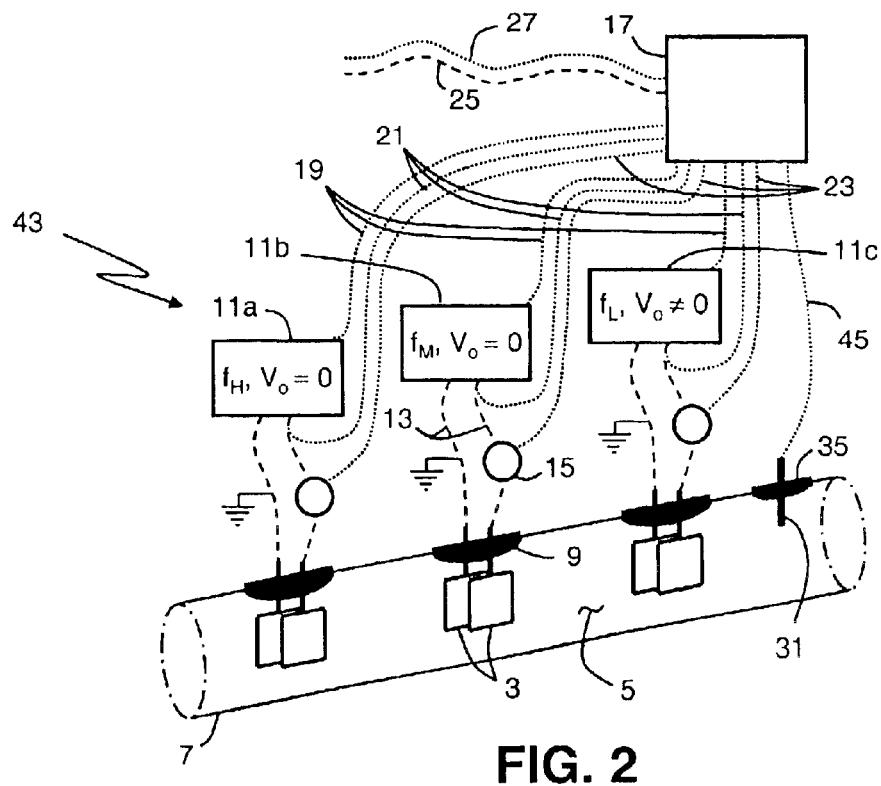
FIG. 2 is a schematic representation of an apparatus, wherein the fluid temperature is monitored but not controlled.

FIG. 2 is a schematic illustration of another apparatus 43 that can be used to collect appropriate data for another embodiment of the current invention. Apparatus 43 includes three pairs of electrodes 3 immersed in highly resistive fluid 5 flowing in conduit 7. The pairs of electrodes 3 are fixedly held in and electrically isolated from conduit 7 by mounts 9. Apparatus 43 also includes three signal generators 11a, 11b, 11c applying signals ($f_H$,$V_o$=0), ($f_M$,$V_o$=0) and ($f_I$,$V_o$≠0) where $f_H$>$f_M$>$f_L$ through electrical conduits 13 to associated pairs of electrodes 3. One electrical conduit 13 of signal generators 11a, 11b, 11c is grounded for a voltage reference and the other conduit includes a current sensor 15 that measures electrical current flow through the conduit. Apparatus 43 includes thermocouple 31 immersed in fluid 5 and fixedly held in conduit 7 by mount 35. Apparatus 43 further includes controller 17 with electrical conduits 19 for powering each signal generator 13, electrical conduits 21 for monitoring output voltage of each signal generator 13, electrical conduits 23 for monitoring current flow measured by each current sensor 15, and electrical conduit 45 for monitoring the temperature of fluid 5 measured by thermocouple 31. Controller 17 also has electrical conduit 25 to receive power and electrical conduit 27 to communicate information. Unlike apparatus 1 of FIG. 1, apparatus 43 does not include means for maintaining the temperature of fluid 5.

In operation, fluid 5 flows through conduit 7 and between pairs of electrodes 3, power is applied to controller 17 through electrical conduit 25. When used with a method of this invention, the method determines when controller 17 powers signal generators 11a, 11b, 11c to apply signal through conduits 13 and pairs of electrodes 3 to fluid 5. The electrical response of fluid 5 to the applied signals causes current to flow and to be measured by current sensors 15. Controller 17 monitors the applied signals and the corresponding current flows through electrical conduits 19, 21 respectively and compares magnitude and phase of the voltage and current signals to calculate electrochemical impedance of fluid 5 at the three applied signals ($f_H$,$V_o$=0), ($f_M$,$V_o$=0) and ($f_I$,$V_o$≠0). Controller 17 also monitors thermocouple 31 through electrical conduit 45 to determine temperature of fluid 5. A method of this invention uses the impedance data to determine quality and/or condition of fluid 5 and can communicate information about that determination from controller 17 through electrical conduit 27. Controller 17 can receive information used in the method of this invention through electrical conduit 27, for example, information that an essentially complete fluid exchange has occurred or information that updates formulae or look-up tables for converting variable temperature data to constant temperature data can be received. A method of this invention can communicate information about the fluid quality and/or condition determination from controller 17 through electrical conduit 27. The fluid quality and/or condition information can be immediately communicated to a signaling device, for example a warning light, to alert an equipment operator, to a central maintenance facility to notify maintenance personnel when fluid maintenance is needed, or to a device that can turn equipment using the fluid "off" to prevent damage. The fluid quality and/or condition information can be communicated from stored memory when queried by, for example, a service technician's diagnostics system.

While FIG. 2 shows apparatus 43 that monitors fluid response to applied high-, medium- and low-frequency signals, the present invention can, for fluids in applications where changes in the fluid's high frequency response is substantially less significant than the changes in the fluid's medium- and low-frequency responses, use apparatus that monitors fluid response to only medium- and low-frequency signals. In that case, an apparatus would not need signal generator 11a and associated electrodes 3, current sensor 15 and electrical conduits 13, 19, 21, 25 shown in FIG. 2.

As described for apparatus 1 of FIG. 1, apparatus 43 of FIG. 2 can be mounted in locations other than conduit 7 as long as fluid 5 flows between electrode pairs 3 in a manner that allows the fluid between the electrode pairs to be at the temperature measured by thermocouple 31 and representative of the current quality/condition of the fluid in the equipment being monitored. A fewer number of signal generators 11a, 11b, 11c and pairs of electrodes 3 can be used if a signal generator can be controlled to apply multiple desired frequencies and/or offset-voltages. The electrodes 3 need not be flat plates with only one surface of each electrode opposed to the other electrode. An apparatus embodiment can have electrodes geometries with greater than one surface of each electrode opposed to the other electrode. Apparatus 43 can be individual components, as shown in FIG. 2, or can be integrated components, which, for example, reduce cost, size and/or power requirements of the apparatus.

Figure 3:
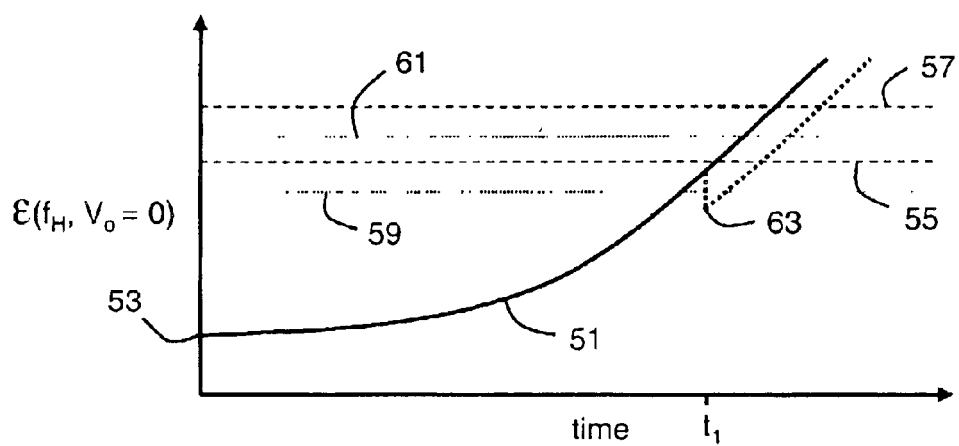
FIG. 3 is a schematic graphic representation of the dielectric (∈) response of a typical transportation or industrial fluid to an applied high-frequency signal with zero offset-voltage as a function of time in use.

FIG. 3 shows the dielectric ($\in$) response 51 of a typical transportation or industrial fluid to an applied high frequency signal ($f_H$) with zero offset-voltage ($V_o$=0) at a fixed temperature as a function of the length of time of equipment operation since the last fluid change. The actual frequency used for the measurement is a function of apparatus electrode geometry, fluid temperature or temperature range, and chemical composition of the fluid being monitored. The required frequency increases as a function of the electrode area divided by the electrode separation. The frequency also increases as a function of the temperature of the fluid. The frequency variation as a function of fluid chemical composition is quite complex and is often determined on a fluid-by-fluid basis. In general, however, for a typical organic based fluid, at a typical operating temperature (in the range of 40° C. to 120° C.), and using parallel-plate electrodes with an area to gap ratio of 300 cm, $f_H$ is on the order of 1 MHz. In general, $f_H$ is typically in the range of about 10 kHz to 10 MHz.

Referring to FIG. 3, the fluid dielectric response 51 in an equipment has initial value 53 just after fresh, that is, unused, fluid has just been added to the equipment during an essentially complete fluid change. As the fluid ages with equipment use, the fluid's dielectric response increases, relatively slowly at first and more rapidly with age. When the fluid's dielectric response exceeds a threshold 55, the fluid condition has degraded to the point that the fluid should be changed soon, and when the dielectric exceeds a second threshold 57 the fluid has reached the end of its useful life and should be changed now or a as soon as is operationally possible to protect the service life of the equipment. In general, appropriate thresholds 55 and 57 are each set as a ratio to the fluid's initial dielectric 51, that is, threshold dielectrics 55, 57 are defined values times the fluid's initial dielectric 51. The defined threshold values are set as a function of the fluid quality where higher quality fluids would have higher thresholds. For example, thresholds 55, 57 could be for a premium, i.e. a relatively higher quality, fluid, whereas thresholds 59, 61 could be for a standard fluid.

Also shown in FIG. 3 is the effect on total fluid dielectric when a volume of fresh fluid is added to the equipment at time $t_1$. The total fluid dielectric 63 at time $t_1$ decreases due to the fluid addition. Typically such fluid additions are a relatively small percentage (<25%) of the total fluid volume in the equipment to compensate for fluid loss or consumption during equipment operation. The change in dielectric caused by the fluid addition is a function of the volume-percent of fluid added, the initial dielectric of the fluid added relative to the initial dielectric of the fluid already in the equipment, and the current condition of the fluid in the equipment. A fluid addition later in a fluid's use cycle will generally reduce the total fluid dielectric more than an addition made early in a fluid's use cycle. In any case, a fluid addition extends the useful life of the total fluid in the equipment. Indeed, if the fluid shown in FIG. 3 is a standard quality fluid, at time $t_1$ the fluid response already exceeds first threshold 59 indicating that the fluid should be changed soon. With the fluid addition at time $t_1$, however, the fluid's dielectric 63 is sufficiently reduced such that the equipment can provide additional service before the "Change Fluid Soon" threshold 59 is again exceeded.

Figure 4:
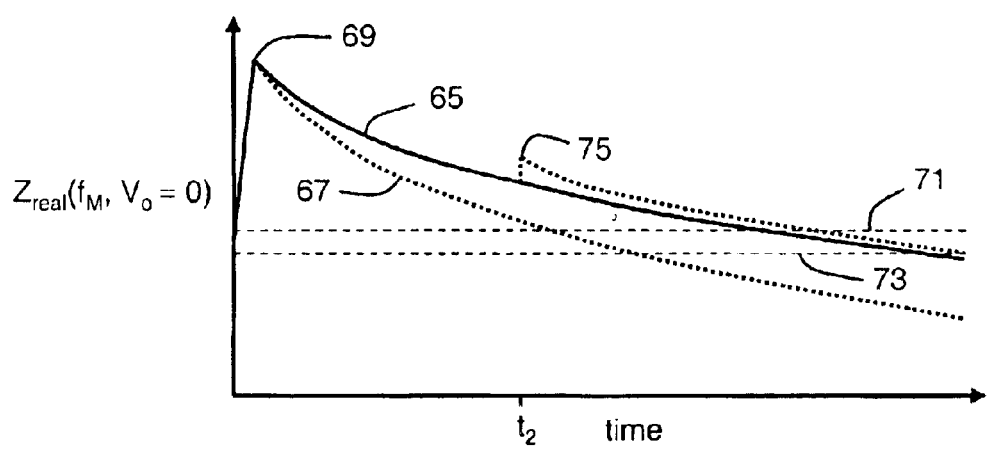
FIG. 4 is a schematic graphic representation of the real impedance ($Z_{real}$) response of a typical transportation or industrial fluid to an applied medium-frequency signal with zero offset-voltage as a function of time in use.

FIG. 4 shows the real impedance ($Z_{real}$) response, for two typical transportation or industrial fluids, to an applied medium frequency signal ($f_M$) with zero offset-voltage ($V_o$=0) at a fixed temperature as a function of the length of time of equipment operation since the last fluid change. Curve 65 is for a premium or higher quality fluid, i.e. a fluid formulated for extended service in defined test sequence, whereas curve 67 is for a standard or relatively lower quality fluid, i.e. a fluid formulated for standard service in the same test sequence. The medium frequency required for the curves shown in FIG. 4 is a function of apparatus electrode geometry, fluid temperature or temperature range, and chemical composition of the fluid being monitored, with the same functional dependencies as for the high frequency ($f_H$) needed for FIG. 3. For a typical organic based fluid, with common performance additives, at a typical operating temperature (in the range of 40° C. to 120° C.), and using parallel-plate electrodes with an area to gap ratio of 300 cm, $f_M$ is on the order of 100 Hz. In general, $f_M$ is typically in the range of about 1 Hz to 500 kHz.

Referring to FIG. 4, a fluid's real-impedance response 65, 67 rises relatively quickly, as a function of equipment use, to a maximum value ($M_M$) 69. The value of the peak 69 is not as critical to the useful life of the fluid as is the percent decrease from this peak value during fluid life. Curves 65 and 67 are scaled to have the same peak value 69. During the same use, the real-impedance of both the premium and standard quality fluids decrease as a function of time, with the standard fluid decreasing more rapidly. When either fluid's real-impedance decreases below a threshold 71, the fluid condition has degraded to the point that the fluid should be changed soon, and when the real-impedance decreases below a second threshold 73, the fluid has reached the end of its useful life and should be changed now or as soon as operationally possible to protect the service life of the equipment. In general, appropriate thresholds are set such that the ratios of the threshold-real-impedance to the fluid's peak-real-impedance are defined values independent of the quality of the fluid.

Also shown in FIG. 4 is the affect on total fluid real-impedance when a volume of fresh fluid is added to the equipment at time $t_2$. The post-addition real-impedance 75 increases as a function of the volume-percent of the fluid addition, the peak real-impedance of the fluid added relative to the peak real impedance of the fluid already in the equipment, and the current condition of the fluid in the equipment. A fluid added later in a fluid's use cycle will generally increase the total fluid real-impedance more than an addition made early in a fluid's use cycle. In any case, a fluid addition, to either a fluid with curve 65 or 67, extends the useful life of the total fluid in the equipment.

Figure 5:
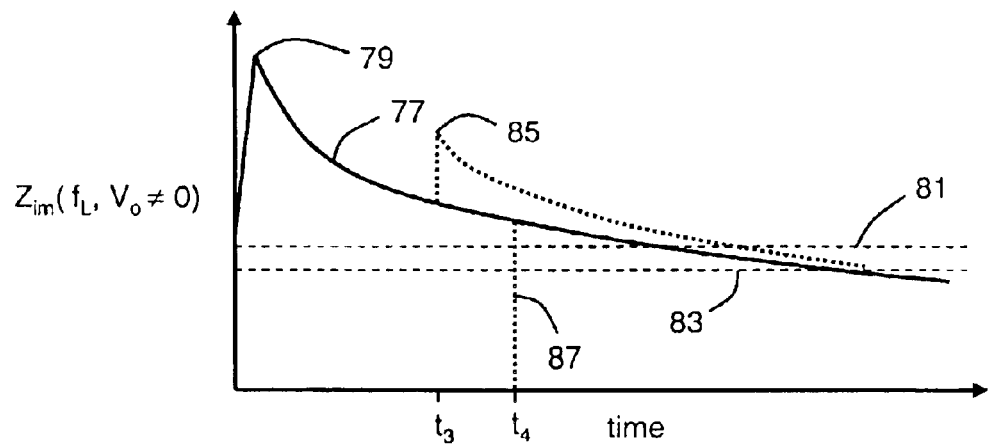
FIG. 5 is a schematic graphic representation of the imaginary impedance ($Z_{im}$) response of a typical transportation or industrial fluid to an applied low-frequency signal with a non-zero offset-voltage as a function of time in use.

FIG. 5 shows the imaginary impedance ($Z_{im}$) response 77, for a typical transportation or industrial fluid, to an applied low-frequency signal ($f_L$) with non-zero offset-voltage ($V_o \neq 0$) at a fixed temperature as a function of equipment use since the last fluid change. As with both the high and medium frequencies, the low frequency required for curve 77 is a function of apparatus electrode geometry, fluid temperature or temperature range and chemical composition of the fluid being monitored. In general, however, for a typical organic based fluid, with common general, however, for a typical organic based fluid, with common performance additives, at a typical operating temperature (in the range of 40° C. to 120° C.), and using parallel plate electrodes with an area to gap ratio of 300 cm, $f_L$ is on the order of 1 Hz. In general, $f_L$ is typically in the range of about 10 mHz to 10 Hz. Similarly, the required offset-voltage is primarily a function of the chemical composition of the fluid being monitored, and is, in general, in the range of 500 mV to 6 V.

Referring to FIG. 5, a fluid's imaginary impedance response 77 rises quickly, as a function of equipment use, to a maximum value ($M_L$) 79, after which the response decreases quickly at first, then less quickly, during fluid use. The value of the peak 79 is not as critical to the useful life of the fluid as is the percent decrease from this peak value during fluid life. When the fluid's imaginary-impedance decreases below a threshold 81, the fluid condition has degraded to the point that the fluid should be changed soon, and when the imaginary-impedance decreases below a second threshold 73 the fluid has reached the end of its useful life and should be changed now or as soon as operationally possible to protect the service life of the equipment. In general, appropriate thresholds are set such that the ratios of the threshold-imaginary-impedance to the fluid's peak-imaginary-impedance are defined values independent of the quality of the fluid.

Also shown in FIG. 5 is the affect on total fluid imaginary-impedance when a volume of fresh fluid is added to the equipment at time $t_3$, where the post-addition imaginary-impedance 85 has increased. The change in the low-frequency imaginary-impedance is a function of the volume-percent of the fluid addition, the peak imaginary-impedance of the fluid added relative to the peak imaginary-impedance of the fluid already in the equipment, and the current condition of the fluid in the equipment. However, unlike the high-frequency dielectric and medium-frequency real-impedance responses where a fluid addition made later in a fluid's use cycle shows a greater change, the low-frequency imaginary-impedance shows a greater change when the fluid addition is made earlier in the fluid's use cycle.

FIG. 5 further shows the effect of polar-coolant contamination, for example water, on a fluid's imaginary-impedance. At time $t_4$ a leak occurred such that coolant used in the equipment contaminated the fluid of FIG. 5. A coolant contamination on the order of one volume-percent is typically sufficient to decrease a fluid's imaginary-impedance to below the "Change Fluid Now" threshold 83.

The change in a fluid's electrical responses as a function of actual time, what would typically be used as the X-axis for in FIGS. 3, 4, 5, at high, medium and low frequencies is highly dependent not only on the particular fluid, but also on the equipment in which the fluid is used and the operation variables of the equipment. As an example, two equipment of different design (or of different age and performance condition) performing the same operation can find one equipment stressing the fluid so that the low-frequency dielectric response crosses the "Change Fluid Soon" threshold (threshold 81 in FIG. 5) before the fluid's high- or medium-frequency response crosses a threshold; while the other equipment stresses the same fluid so that the medium-frequency dielectric response crosses the "Change Fluid Soon" threshold (threshold 71 in FIG. 4) first. As another example, two identical equipment operated differently, one operating under intermittent light load and one operating under continuous heavy load, can find the medium-frequency response threshold crossed first for one operating condition and the low-frequency response threshold crossed first for the other operation condition.

Hence, in general a fluid's response is preferably monitored at all three applied signals ($f_H, V_o = 0$), ($f_M, V_o = 0$), ($f_L, V_o \neq 0$) to properly determine fluid condition under all possible variables of equipment design, condition or operation. There are, however, fluids in applications where change in the fluid's high-frequency response is substantially less significant than the changes in the fluid's medium and low frequency responses. That is, for fluids in those applications if FIGS. 3, 4, 5 were scaled to the same "use" axis, i.e. X-axis, only the very initial portion of FIG. 3 would be shown with the fluid's high-frequency dielectric response showing little rise while both the fluid's medium-frequency real impedance and low-frequency imaginary impedance responses showing changes similar to FIGS. 4 and 5. In those fluid applications, a fluid's response need only be monitored at medium and low frequency ($f_M, V_o = 0$), ($f_L, V_o \neq 0$) to properly determine fluid condition.

FIGS. 3, 4, 5 show fluid response at fixed fluid temperature. Fluid response, however, at any of the frequencies is temperature dependent. For certain fluids in particular applications, variation in fluid response over an equipment's operating temperature range can be greater than the change in a fluid's response at fixed temperature between initial or peak values and the thresholds for "Change Fluid Soon" or "Change Fluid Now". Hence, where an equipment's fluid-operating-temperature range may be large, to accurately determine the condition of the fluid in an essentially continuous manner, either the measurement apparatus must have means for controlling the fluid temperature, as apparatus 1 in FIG. 1, or must have a means for measuring the fluid temperature, as apparatus 43 in FIG. 2, so that a method of this invention can compensate or correct for changes in fluid temperature.

Figure 6:
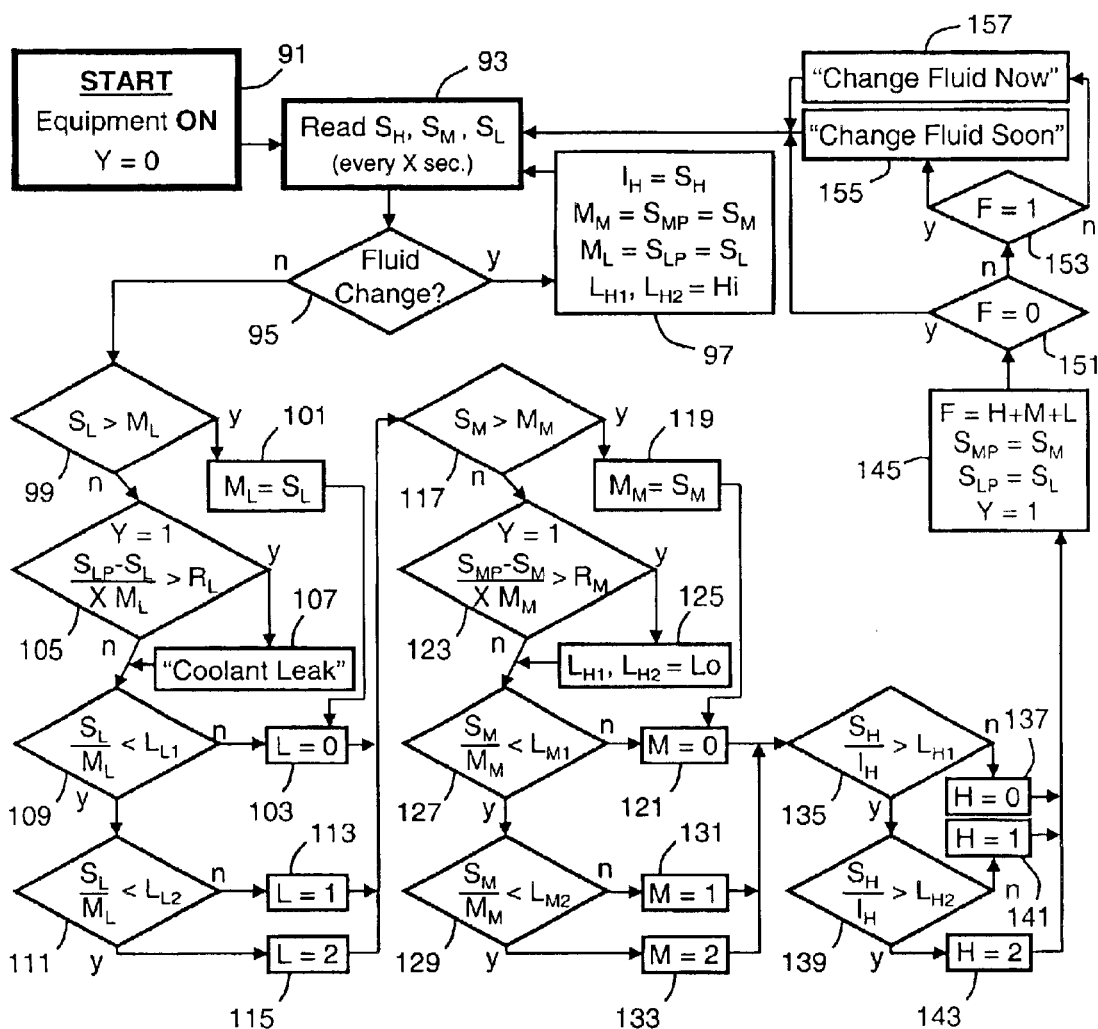
FIG. 6 is a flow chart of a feature of the present invention using high-, medium- and low-frequency fluid response data obtained at fixed fluid temperature to determine fluid quality and condition.

FIG. 6 shows a first embodiment of a feature of the present invention that uses a fluid's response to the above described high-, medium- and low-frequency signals to determine the quality and condition of a fluid in equipment where the fluid is maintained at constant temperature for condition determination. Constant temperature can be maintained either by the fluid measurement apparatus, for example apparatus 1 in FIG. 1, or by the equipment or a means associated with the equipment in which the fluid is used.

Referring to FIG. 6, the method begins in block 91 each time the equipment is started, i.e. turned "on". A variable "Y" is set equal to zero, and the method proceeds to block 93 to read fluid responses, $S_H$, $S_M$ and $S_L$, to high-, medium- and low-frequency signals respectively, which are obtained by a fluid measurement apparatus of the type described in association with FIG. 1. $S_H$, $S_M$ and $S_L$ can be dielectric, real-impedance and imaginary impedance responses respectively, as shown in FIGS. 3, 4, 5 respectively, or values that are essentially equivalent. For example, instead of converting the fluid responses to values with appropriate dimensional units, analogue voltages, currents or digital inputs can be read that can be converted to appropriate fluid responses. As another example, in many fluids the magnitude of the fluid's total-impedance ($|Z|$) at the medium frequency is essentially the same as the fluid's real-impedance ($Z_{real}$) due to a fluid's substantially smaller imaginary-impedance ($Z_{im}$); hence, for processing reasons total-impedance may be used. $S_H$, $S_M$ and $S_L$ can be data collected by the apparatus over a short period of time with no filtering, or can be averaged over a longer period of time and filtered to minimize noise and to better quantify a fluid's response to the applied signals. In any case the method reads the data at fixed intervals of "X" seconds to determine fluid quality.

Each time inputs $S_H$, $S_M$ and $S_L$ are read, the method, in block 95, determines if an essentially complete fluid change has been made since the last time the inputs were read. This determination can be based on an input to the method. For example, a maintenance person, or operator, could provide a signal when a fluid change is made that is communicated to the controller (e.g. by electrical conduit 27 to controller 17 of apparatus 1 in FIG. 1) and detected in block 95. As another example, a sensor or sensor system that detects fluid change either by fluid level changes or by other means could provide a signal that is detected in block 95. The determination of block 95 can also be made by a subroutine that uses inputs $S_H$, $S_M$ and $S_L$ and no additional input to identify the fluid change. An example of such a subroutine will be discussed later in conjunction with FIG. 11. In any case, if the determination in block 95 is "yes", then in block 97 the initial value $I_H$ for the high-frequency determination (corresponding to point 53 in FIG. 3) is set equal to $S_H$, and the maximum values $M_M$, $M_L$ for the medium- and low-frequency determinations respectively (corresponding to points 69, 79 in FIGS. 4, 5 respectively) are set equal to $S_M$, $S_L$ respectively as starting points for determining the actual $M_M$ and $M_L$, since the $S_M$, $S_H$ immediately after a fluid change are known to be less than what will to be the respective maximum values as the fresh fluid is used in the equipment. Also in block 97, the values of the medium- and low-frequency response read in the previous fluid quality/condition determination, $S_{MP}$, $S_{LP}$, are set equal to $S_M$, $S_L$ respectively since the previously stored values are not relevant in determining the fresh fluid's quality or condition. Also in block 97 the thresholds for the high-frequency fluid determination $L_{H1}$, $L_{H2}$ are set to "Hi" values (corresponding to thresholds 55, 57 respectively in FIG. 3) assuming that the fresh fluid is a premium quality fluid; an assumption that is tested later in the method. After block 97, the method returns to block 93 where X seconds after the previous reading, $S_H$, $S_M$, $S_L$ are again read.

If the determination in block 95 is "no", the method advances to block 99 which determines if the low-frequency response $S_L$ is greater than a stored maximum low-frequency response $M_L$. If the answer is "yes", which means that the low-frequency response has not reached its maximum value, than $M_L$ is replaced by $S_L$ in block 101 and no further analysis of the low-frequency response is done with the method advancing to block 103 where variable "L" is set equal to zero to indicate that the fluid condition, determined by the fluid's low-frequency response, is acceptable. If the answer to block 99 is "no", i.e. $S_L$ is no longer increasing, block 105 determines if the relative rate of decrease of $S_L$ is greater than a predetermined rate $R_L$. The relative rate of low-frequency response change is the low-frequency response from the previous iteration of the method $S_{LP}$ minus the low frequency response of the current iteration $S_L$, divided by the maximum value $M_L$ and by the time between the iterations, which, except for the first iteration after equipment start, equals X. To ignore the rate determination during the first iteration after equipment start, block 105 also determines if Y=1. If the determination of block 105 is "yes", that is the relative rate of $S_L$ decrease is greater than $R_L$ and this is not the first iteration after equipment start, there is high probability that coolant is leaking into the fluid being monitored, and in block 107 a "Coolant Leak" warning is sent. The warning may be sent to memory for later retrieval, to a signaling device, for example a warning light, to alert an equipment operator, to a central maintenance facility to notify maintenance personnel, or a device to turn the equipment "off" to prevent equipment damage.

If the determination in block 105 is "no", or after the warning is given in block 107, a determination is made in block 109 whether the low-frequency response $S_L$ divided by the maximum value $M_L$ is below a first threshold $L_{L1}$. If the block 109 determination is "no", the variable "L" is set equal to zero to indicate that the fluid condition determined by the fluid's low-frequency response is acceptable. If the block 109 determination is "yes", a determination is made in block 111 whether the low-frequency response $S_L$ divided by the maximum value $M_L$ is below a second threshold $L_{L2}$. If the block 113 determination is "no", "L" is set equal to one to indicate that, based on the low-frequency response, the fluid should be changed soon, and if the block 113 determination is "yes", "L" is set equal to two in block 115 to indicate that, based on the low-frequency response, the fluid should be changed now.

After a value for "L" is assigned in block 103, 113 or 115, the method in block 117 determines if the medium-frequency response $S_M$ is greater than a stored maximum medium-frequency response $M_M$. If the answer is "yes", which means that the medium-frequency response has not reached its maximum value, than $M_M$ is replaced by $S_M$ in block 119 and no further analysis of the medium-frequency response is done with the method advancing to block 121 where variable "M" is set equal to zero to indicate that the fluid condition determined by the fluid's medium-frequency response is acceptable. If the block 117 determination is "no", i.e. $S_M$ is no longer increasing, block 123 determines if the relative rate of decrease of $S_M$ is greater than a predetermined rate $R_M$. The relative rate of medium frequency change is the medium-frequency response from the previous iteration of the method $S_{MP}$ minus the medium-frequency response of the current iteration $S_M$, divided by the maximum value $M_M$ and by the time between the iterations, which, except for the first iteration after equipment start, equals X. As in block 105, block 123 also determines if Y=1 so as to ignore the rate determination during the first iteration of the method after equipment start. If the block 123 determination is "yes", that is the relative rate of $S_M$ decrease is greater than $R_M$ and this is not the first iteration after equipment start, there is high probability that the fluid is of a relatively low quality and in block 125 the thresholds for the high-frequency fluid determination $L_{H1}$, $L_{H2}$, which will be used until the next essentially complete fluid change, are set equal to "Lo" values (corresponding to thresholds 59, 61 respectively in FIG. 3).

If the block 123 determination is "no" or after thresholds $L_{H1}$, $L_{H2}$ are set to "Lo" values in block 125, a determination is made in block 127 whether the medium-frequency response $S_M$ divided by the maximum value $M_M$ is below a first threshold $L_{M1}$. If the determination is "no", the variable "M" is set equal to zero in block 121 to indicate that the fluid condition, determined by the medium-frequency response, is acceptable. If the block 127 determination is "yes", a determination is made in block 129 whether the medium-frequency response $S_M$ divided by the maximum value $M_M$ is below a second threshold $L_{M2}$. If the determination is "no", "M" is set equal to one in block 131 to indicate that, based on the medium-frequency response, the fluid should be changed soon, and if the block 129 determination is "yes", "M" is set equal to two in block 133 to indicate that, based on the medium-frequency response, the fluid should be changed now.

After a value for "M" is assigned in block 121, 131 or 133, the method in block 135 determines whether the high-frequency response $S_H$ divided by $I_H$, the initial high-frequency response when the fluid was fresh, is above a first threshold $L_{H1}$. If the determination is "no", the variable "H" is set equal to zero in block 137 to indicate that the fluid condition, determined by the high-frequency response, is acceptable. If the block 135 determination is "yes", a determination is made in block 139 whether the high-frequency response $S_H$ divided by $I_H$ is above a second threshold $L_{H2}$. If the determination is "no", "H" is set equal to one in block 141 to indicate that, based on the high-frequency response, the fluid should be changed soon, and if the block 139 determination is "yes", "H" is set equal to two in block 143 to indicate that, based on the high-frequency response, the fluid should be changed now.

After the value for "H" is assigned in block 137, 141 or 143, the method in block 145 sets variable "F" equal to the sum of variables "H", "M" and "L", sets the previous medium- and low-frequencies response values, $S_{MP}$, $S_{LP}$ respectively, to the current values, and sets variable "Y" equal to one so that the method in blocks 105 and 123 knows that the next iteration is not the first iteration after equipment start. The method then determines in block 151 if the variable "F" equals 0. If the determination is "yes", which means that the fluid condition determined by each the high-, medium- and low-frequency responses is acceptable, the method returns to block 93 where X seconds after the previous reading, $S_H$, $S_M$, $S_L$ are again read and the method repeated. If the block 151 determination is "no", then in block 153 the determination is made whether variable "F" equals 1. If the determination is "yes", which means that the fluid condition determined by one of the high-, medium- and low-frequency responses was that the fluid should be changed soon, the method advances to block 155 where a "Change Fluid Soon" warning is sent. The warning may be sent to memory for later retrieval, to a signaling device, for example a warning light, that can alert an equipment operator, or to a central maintenance facility to notify maintenance personnel. If the block 153 determination is "no", since block 151 determined that "F" is not equal to 0, then "F" must be greater-than- or equal-to 2, which means that the fluid condition determined by at least two of the high-, medium- and low-frequency responses was that the fluid should be changed soon, or that the fluid condition determined by at least one of the responses was that the fluid should be changed now, the method advances to block 157 where a "Change Fluid Now" warning is sent. As with a "Change Fluid Soon" warning, the warning is sent to an appropriate location using an appropriate means, for example electrical conduit 27 of controller 17 of apparatus 1 in FIG. 1. After a warning is sent in either block 155 or block 157, the method returns to block 93 where X seconds after the previous reading, $S_H$, $S_M$, $S_L$ are again read and the method repeated. The method continues to repeat until the equipment using the fluid is turned "off".

In this manner, the method essentially continuously monitors the condition of a fluid and sends warnings when fluid condition exceeds thresholds. Also the method determines fluid quality to set the thresholds for the high-frequency fluid condition determination and monitors the relative rate of decrease of the low-frequency response to determine if a coolant may be leaking into the fluid.

The embodiment of FIG. 6 has the fluid responses $S_H$, $S_M$, $S_L$ being read immediately after the equipment using the fluid is turned "on". While the embodiment is for monitoring fluids maintained at constant temperature, there may be applications/equipment where some equipment operation time is needed before the fluid reaches constant temperature. For such applications/equipment, an embodiment similar to that of FIG. 6 can include a step between blocks 93, 95 where after the equipment is turned "on" the method does not advance to block 95 until the fluid reaches a desired fluid temperature. Such a block will be shown in the embodiment of FIG. 9.

As previously discussed in conjunction with FIGS. 3, 4, 5, there are fluids in applications where, with a very high level of confidence, the change in the fluid's high-frequency response is substantially less significant than the fluid's medium and low frequency responses. For those cases the method of FIG. 6 would always determine in block 135 that the relative high-frequency response ($S_H/I_H$) is always less than threshold $L_{H1}$ when both the relative low- and medium-frequency responses ($S_L/M_L$, $S_M/M_M$) cross the first thresholds ($L_{L1}$, $L_{M1}$ respectively) or when one of the responses crosses the second threshold ($L_{L2}$, $L_{M2}$ respectively). Hence, for fluids in such applications, an embodiment of the invention need not monitor the high-frequency response to determine fluid condition.

Figure 7:
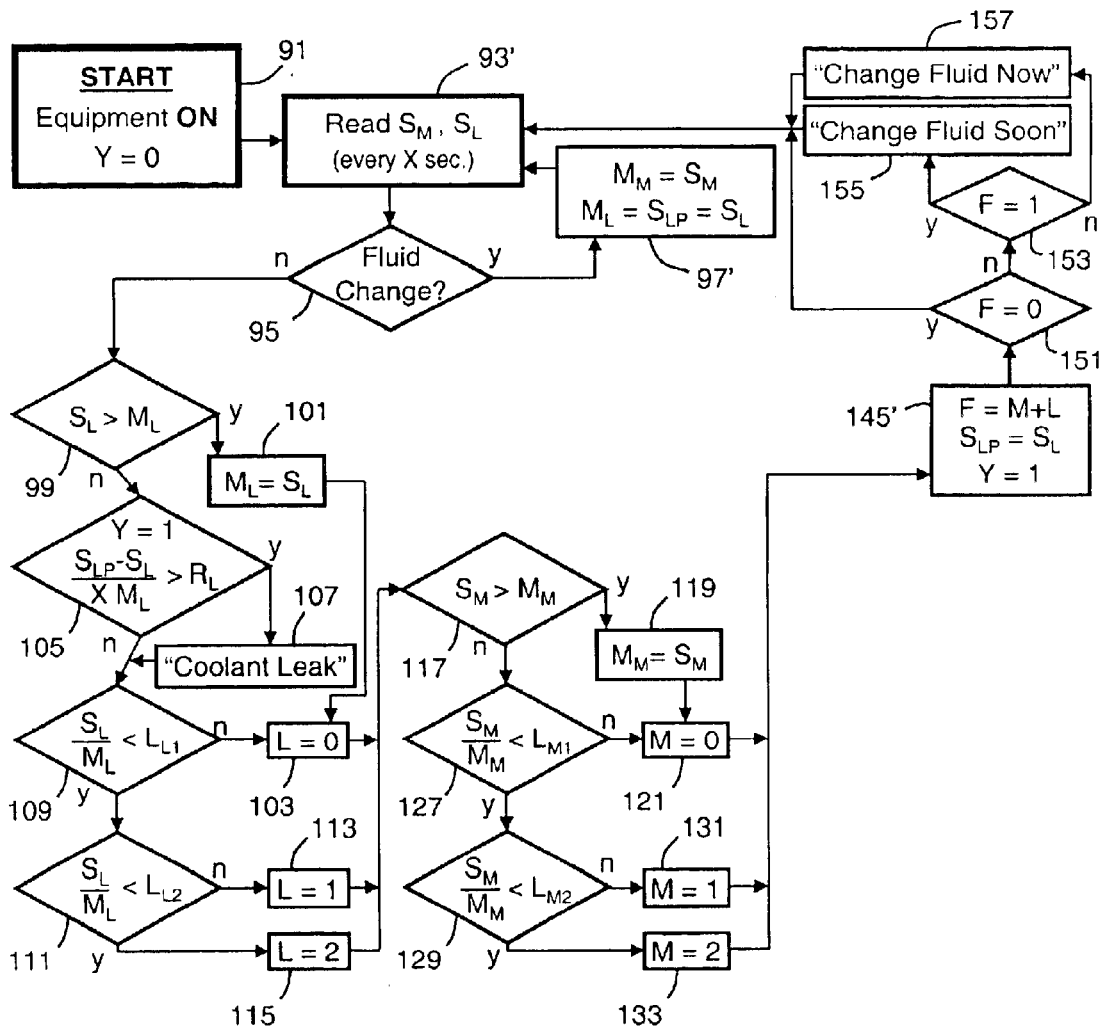
FIG. 7 is a flow chart of a feature present invention using medium- and low-frequency fluid response data obtained at fixed fluid temperature to determine fluid quality and condition.

FIG. 7 shows an embodiment of a feature of the present invention for use in determining the condition of a fluid in equipment where change in the fluid's high-frequency response is substantially less significant than the fluid's medium- and low-frequency responses, and where the fluid is maintained at constant temperature for condition determination. Since the method is quite similar to the method of FIG. 6, equivalent blocks are labeled the same.

Referring to FIG. 7, the method again begins in block 91 when the equipment is turned "on" and Y is set equal to zero. In block 93', only fluid responses $S_M$ and $S_L$ are read and in block 95 if the determination is that an essentially complete fluid change has been made while the equipment was "off", in block 97', only $M_M$ is set equal to $S_M$, and $M_L$ and $S_{LP}$ are set equal to $S_L$ since unlike block 97 of the method in FIG. 6, the initial value $I_H$ and the thresholds for the high-frequency response $L_{H1}$, $L_{H2}$ are not need for a high-frequency fluid condition determination, and $S_{MP}$ is not needed for a determination of the relative rate of medium-frequency response change to set thresholds for the high-frequency response.

With continued reference to FIG. 7, if the block 95 determination is "no", then in blocks 99 through 115, the fluid's low-frequency response $S_L$ is used to determine and warn if a coolant leak exists and to set variable "L" in the same manner as the method of FIG. 6, and in blocks 117 through 133 uses the fluid's medium frequency response $S_M$ to set variable "M" in the same manner as the method of FIG. 6. The method of FIG. 7 does not have blocks 193 and 195 of the method of FIG. 6 since the method does not have to determine the fluid's relative rate of decrease of $S_M$ to set thresholds for a high-frequency response fluid condition determination in blocks 135 through 143 which are also eliminated in FIG. 7.

In block 145' of FIG. 7, "F" is set equal to the sum of the variables "M" and "L", the previous low-frequency response value $S_{LP}$ set equal to the current low-frequency response $S_L$ and "Y" is set equal to 1 so that the method in block 105 knows that the next iteration is not the first iteration of the equipment after equipment start. The method then determines in block 151 if the variable "F" equals 0. If the determination is "yes", which means that the fluid condition determined by medium- and low-frequency responses is acceptable, the method returns to block 93' where X seconds after the previous reading, $S_M$, $S_L$ are again read and the method repeated. If the block 151 determination is "no", then in block 153 the determination is made whether variable "F" equals 1. If the determination is "yes", which means that the fluid condition determined by one of the medium- and low-frequency responses was that the fluid should be changed soon, the method advances to block 155 where a "Change Fluid Soon" warning is sent. If the block 153 determination is "no", which means that the fluid condition determined by both of the high-, medium- and low-frequency responses was that the fluid should be changed soon, or that the fluid condition determined by at least one of the responses was that the fluid should be changed now, the method advances to block 157 where a "Change Fluid Now" warning is sent. After a warning is sent in either block 155 or block 157, the method returns to block 93 where X seconds after the previous reading, $S_M$, $S_L$ are again read and the method repeated. The method continues to repeat until the equipment using the fluid is turned "off".

Thus, in this manner, the method of FIG. 7 essentially continuously monitors the condition of a fluid and sends warnings by determining when the fluid's low- and medium-frequency responses exceed thresholds and monitors the relative rate of decrease of the low-frequency response to determine if a coolant may be leaking into the fluid.

As with the embodiment of FIG. 6, the embodiment of FIG. 7 is for monitoring fluid that is maintained at constant temperature for the fluid determination. Since the fluid may not be at the desired constant temperature immediately after the equipment is turned "on", an embodiment can include a block between blocks 93' and 95 such that after the equipment is turned "on" the method does not advance to block 95 until the fluid reaches a desired fluid temperature.

Figure 8:
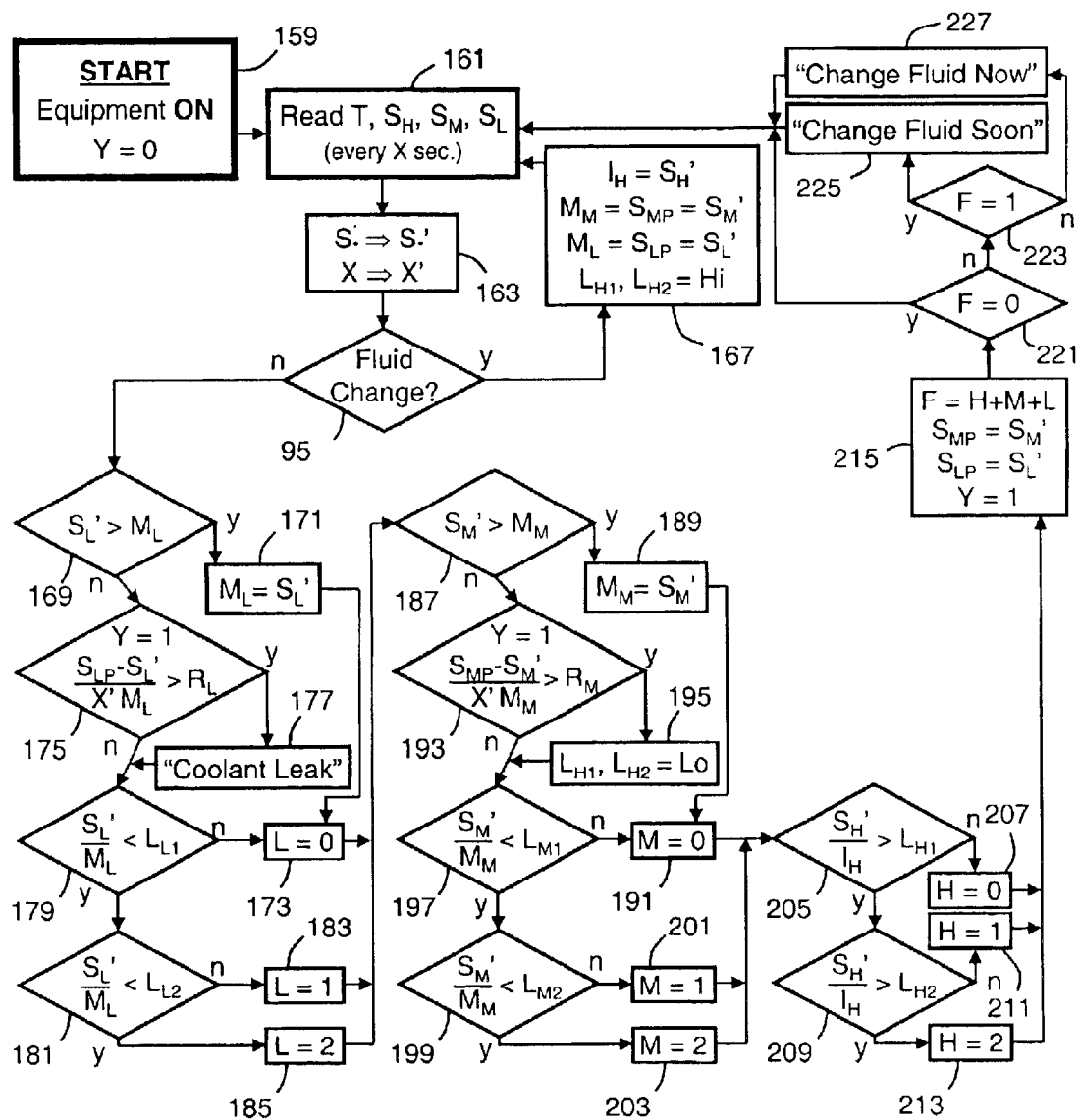
FIG. 8 is a flow chart of a feature of the present invention using high-, medium- and low-frequency fluid response data that are corrected for fluid temperature variations to determine fluid quality and condition.

There are, however, many applications for in-use fluid monitoring where maintaining constant fluid is not practical for cost or other reasons. FIG. 8 shows another embodiment of a feature of the present invention for use in determining the quality and condition of a fluid in equipment where the fluid temperature is not maintained at constant temperature for fluid condition determination. This embodiment is appropriate for use in conjunction with apparatus 43 of FIG. 2.

Referring to FIG. 8, each time the equipment is turned "on", in block 159 the variable "Y" is set equal to zero. The method in block 161 then reads fluid responses $S_H$, $S_M$ and $S_L$ to applied high-, medium- and low-frequencies signals respectively, as previously discussed, and reads the fluid temperature T monitored by the measurement apparatus. Advancing to block 163, the temperature T is used to convert fluid responses $S_H$, $S_M$, $S_L$ read at temperature T to constant temperature fluid responses $S_H'$, $S_M'$, $S_L'$ such that the response variations due to temperature are effectively eliminated or minimized to an acceptable level. The response temperature conversions can be made using predetermined functions or look-up tables. The functions or tables can be permanently fixed in read-only memory, or the embodiment can allow the functions or tables to be updated, if needed, by appropriate means, for example by electrical conduit 27 to controller 17 of apparatus 43 in FIG. 2, to allow for formulation changes of fluid being used in the equipment.

In addition to converting the fluid responses to constant temperature values, the time interval X between reading the fluid responses is corrected to a constant temperature interval X' so that the rates of response change are properly corrected for temperature variations. As with the response conversions, the time interval conversion can be made using a predetermined function or a look-up table that is either permanently fixed in read-only memory or that can be updated if needed. In any case, the embodiment of FIG. 8 determines in block 95 if an essentially complete fluid change has been made since the last iteration and the remaining blocks numbered 167 to 227 are the same as the blocks numbered 97 to 157 of the embodiment of FIG. 6 except that the converted fluid responses $S_H'$, $S_M'$, $S_L'$ and the converted time interval X' are used instead of the read responses $S_H$, $S_M$, $S_L$ and the fixed time interval X.

In this manner, the method essentially continuously monitors the condition of a fluid that varies in temperature. Also, as the fluid temperature varies, the method determines the fluid's quality in order to set the thresholds for the high-frequency fluid condition determination and monitors the relative rate of decrease of the low-frequency response to determine if a coolant may be leaking into the fluid.

While the embodiment of FIG. 8 determines fluid condition using the fluid's high-, medium- and low-frequency responses, there are fluids in applications where the change in the fluid's high-frequency response is substantially less significant than the fluid's medium- and low-frequency response changes. For fluids in such applications, an embodiment could be shown similar to the embodiment of FIG. 8 that allows for variation in fluid temperature but uses only the medium- and low-frequency responses. Such an embodiment would not read $S_H$ and would not include the thresholds, variables and conversions used to determine the fluid's high frequency condition shown FIG. 8.

The embodiment of FIG. 8 determines fluid condition as the fluid varies for any temperature. The response and time interval conversion in block 163, however, is not an exact conversion due to the complex temperature-dependence of a fluid's electrical response. While high conversion accuracy over a wide temperature range is desired, conversion accuracy outside a fluid's typical operating temperature range is sometimes sacrificed to optimize accuracy within the range. In particular, when equipment is turned "on", fluid temperature may be sufficiently outside the typical operating temperature range that the "converted" fluid response may not be meaningful. Hence, an embodiment of the invention can include a step between blocks 159, 161 of FIG. 8 such that after the equipment is turned "on", that prevents the method from advancing to block 163 until the fluid reaches a predetermined temperature range.

Figure 9:
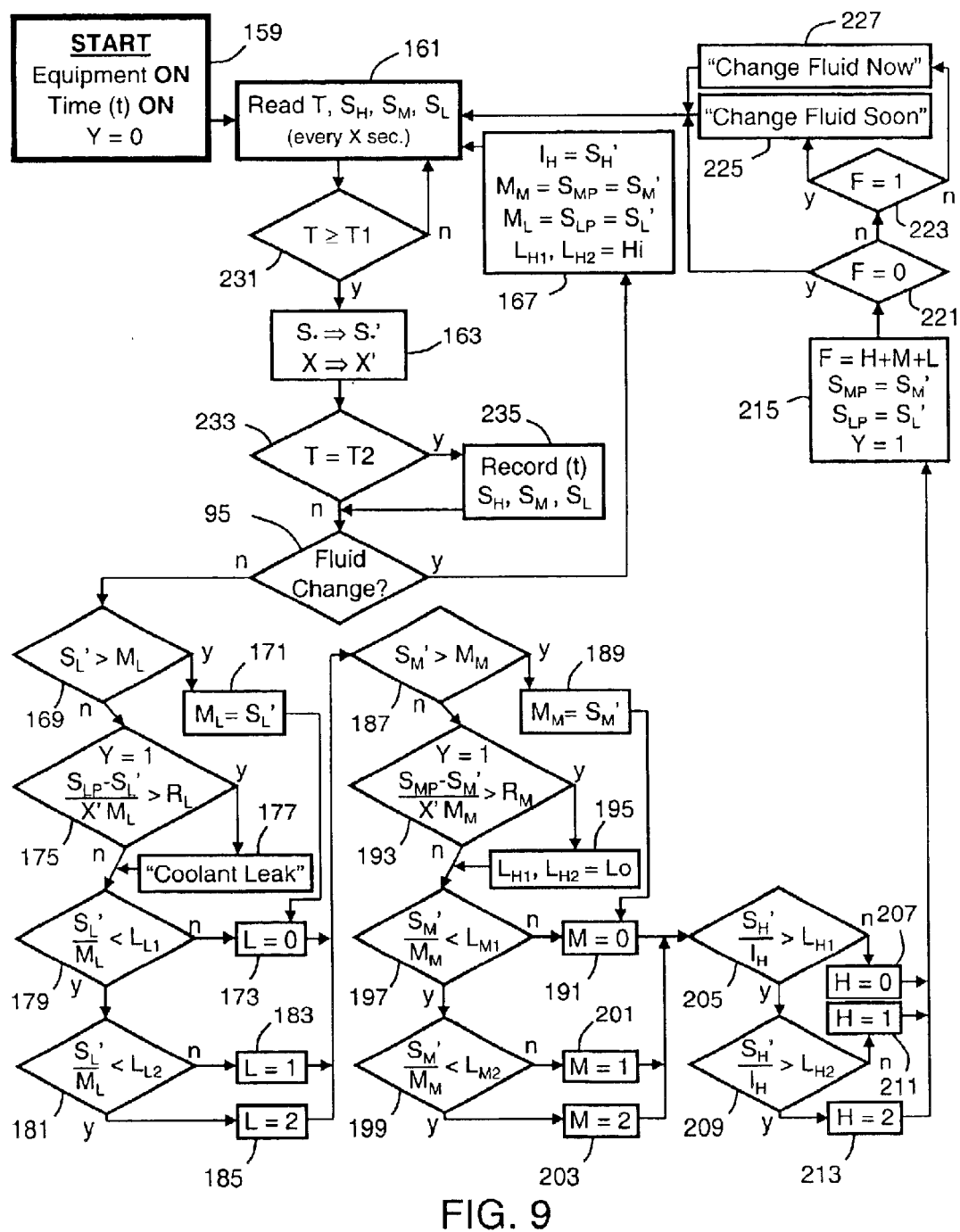
FIG. 9 is a flow chart of a feature of the present invention wherein high-, medium- and low-frequency fluid response data are corrected for fluid temperature variations to determine fluid quality and condition until the fluid temperature exceeds a fixed temperature threshold, and where uncorrected fluid response data are recorded at a fixed temperature.

FIG. 9 shows another embodiment of a feature of the present invention for determining the quality and condition of a fluid using high-, medium- and low-frequency responses in equipment where in addition to converting fluid responses above a fixed first temperature threshold for temperature variations, fluid responses at a second fixed fluid temperature are recorded for possible later or additional analysis of fluid quality and condition. This embodiment is appropriate for use in conjunction with equipment and sensing apparatus where a fluid is not always at constant temperature.

Referring to FIG. 9, as in the embodiment of FIG. 8, each time the equipment is turned "on", the variable "Y" is set equal to zero in block 159, and the method in block 161 reads responses $S_H$, $S_M$ and $S_L$ monitored by an apparatus to respective high-, medium- and low-frequencies signals applied to the fluid by the apparatus, as previously discussed. Also in block 161 the method reads fluid temperature T monitored by the apparatus. Advancing to block 231, the method determines if the fluid temperature T is greater than or equal to a fixed temperature T1. Temperature T1 is selected so that temperature conversion of responses $S_H$, $S_M$ and $S_L$ are known to be meaningfully accurate at this temperature and above. Typically, temperature T1 to be above the highest ambient temperature experienced by the equipment so that after relatively long equipment "off" periods, the fluid temperature is below temperature T1 when the equipment is turned "on". If the block 231 determination is "no", that is the fluid temperature is below preset temperature T1, then the method returns to block 161 and reads $S_H$, $S_M$, $S_L$ and T, X seconds after the previous reading and determines if the fluid temperature T is now at or above preset temperature T1 in block 231. If the determination is again "no" the method continues reading the fluid responses and temperature every X seconds until the block 231 determination is "yes" and the method advances to block 163 where the fluid responses $S_H$, $S_M$ and $S_L$ are converted to constant temperature fluid responses $S_H'$, $S_M'$, $S_L'$ to eliminate or at least minimize to an acceptable level the effects of temperature variation on fluid responses. Also in block 233 the time interval X between reading fluid responses is corrected to a constant temperature interval X' so that the relative rates of response change are properly corrected for temperature variations. As discussed in the embodiment of FIG. 8, the conversions can be made using functions or look-up tables that are either permanent or can be updated to allow for changes in formulation of the fluid being used in the equipment.

With continued reference to FIG. 9, in block 233 the method determines if the fluid temperature T is equal to pre-selected fixed temperature T2 which, in this embodiment, is greater than or equal to T1. If the determination is "yes", the method, in block 235, records the fluid responses $S_H$, $S_M$, $S_L$ and a time "t" that indicates when the data are recorded either in terms of calendar time or in terms of equipment use since the previous data were recorded. The unconverted, fixed-temperature data are recorded in memory for possible additional fluid analysis. Such fluid analysis may be done later when the memory is queried, for example, by a service technician using a service device that can communicate with the memory, to obtain a history of fluid response. Such additional fluid analysis may be done in conjunction with the present invention method to provide, for example, additional fluid condition or quality analysis. The collection of unconverted data at fixed temperature eliminates temperature variability and reduces the memory that would be needed if all data read every X seconds were recorded. After the data are recorded, or if the block 233 determination is "no", the method advances to block 95 where the method determines if an essentially complete fluid change has been made since the last iteration and blocks 167 to 227 are the same as the method embodiment described in FIG. 8.

While the embodiment of FIG. 9 shows temperature T2 being greater than or equal to temperature T1, an embodiment could be shown with blocks 233 and 235 of FIG. 9 placed between blocks 161 and 231 so that temperature T2 can be less than temperature T1. For example, fluid response data recorded in block 235 at a lower temperature T2 may be used in a block, not shown, to determine if coolant is present before the fluid reaches temperature T1.

While the embodiment of FIG. 9 shows fluid response data being recorded for only one fixed temperature, other embodiments can record data at multiple fixed temperatures for a more detailed fluid analysis.

While the embodiment of FIG. 9 uses low-, medium- and high frequency responses to determine fluid quality and conditions, a similar embodiment could be shown where the high-frequency response $S_H$ in not used in the determination for fluids in applications where the change in the fluid's high-frequency response is substantially less significant than the fluid's medium- and low-frequency response changes.

Figure 10:
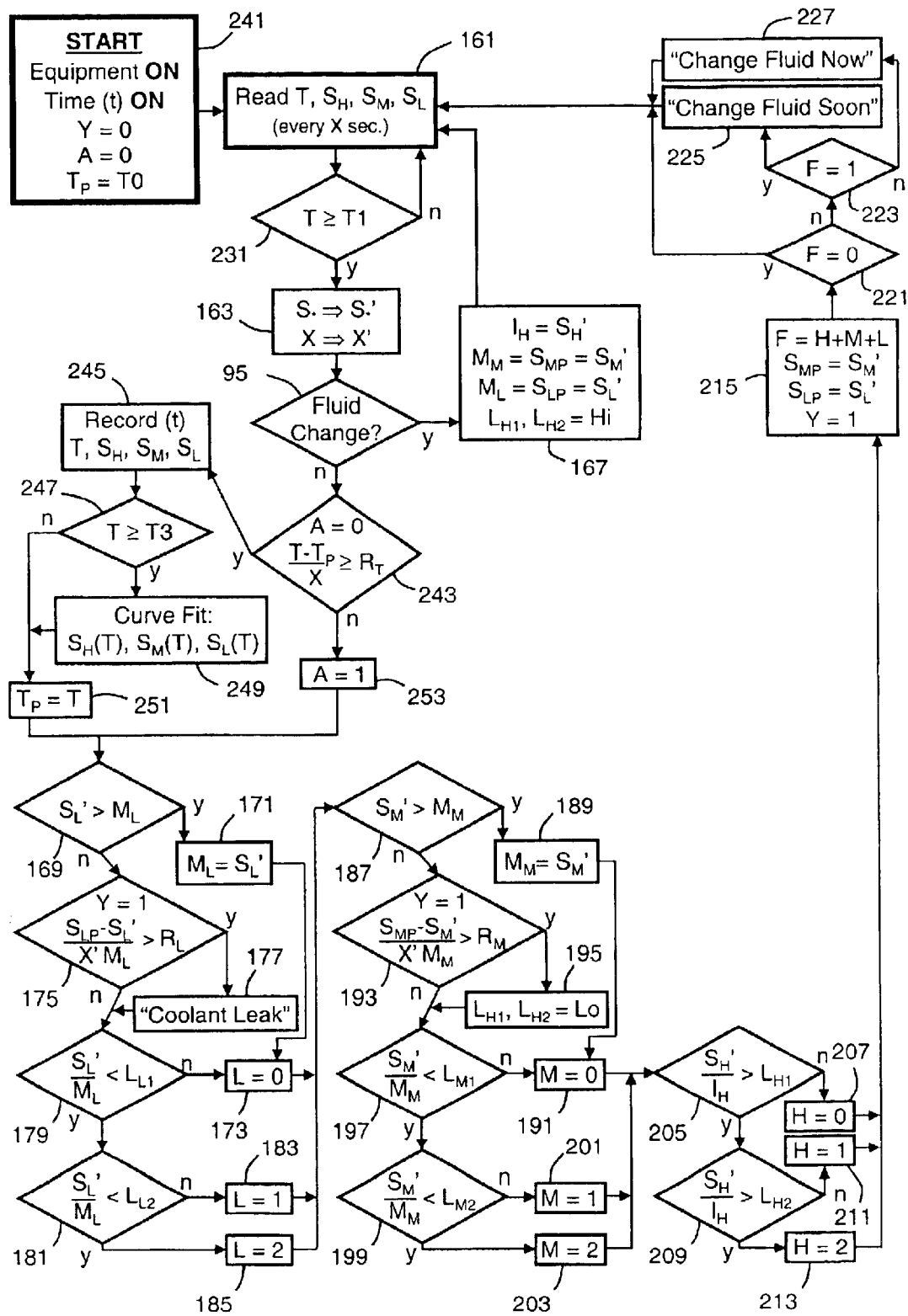
FIG. 10 is a flow chart of a feature of the present invention wherein the functions used to convert or correct fluid response data for fluid temperature variations are determined each time the fluid heats at greater than a fixed rate between two fixed temperatures.

FIG. 10 shows another embodiment of a feature of the present invention for determining the quality and condition of a fluid in equipment where in addition to converting fluid responses above a fixed first temperature threshold to eliminate or minimize effects of temperature variations, the formulae or look-up tables used for the data conversions are updated each time the fluid temperature rises between two temperature thresholds with a rate that is greater than a preset value.

Referring to FIG. 10, when the equipment is turned "on", variables "Y" and "A" are set equal to zero in block 241 and variable $T_P$ is set equal to a fixed number T0, which will be described below. As in other embodiments, the method then in block 161 reads fluid responses $S_H$, $S_M$ and $S_L$ and fluid temperature T. As in the embodiment of FIG. 9, this embodiment in block 231 does not let the method advance to block 163 until the fluid temperature T equals or exceeds fixed temperature T1, which is a temperature above which temperature conversion of responses $S_H$, $S_M$ and $S_L$ are known to be meaningfully accurate. In block 163 the fluid responses and time interval X are converted to constant-temperature responses and time interval that are needed in the fluid quality and condition determination. The response conversions use formulae or look-up tables that the method has stored in memory. In block 95, the method determines if an essentially complete fluid change has occurred to the equipment, and if a change has occurred, the method in block 167 initializes $I_H$, $M_M$, $S_{MP}$, $M_L$, $S_{LP}$, $L_{H1}$ and $L_{H2}$ and returns to block 161 where fluid responses and temperature are again read X seconds after the previous reading. If the block 95 determination is that the fluid has not been changed then the method advances to block 243 where the determination is made if the rate of fluid temperature increase is greater than a fixed rate $R_T$, and if "A" equals zero. The rate of fluid temperature increase is the previous iteration's temperature $T_P$ minus the current temperature T divided by the time interval between the two temperature readings which for iterations other than the first iteration after equipment start is "X". For the first iteration after equipment start, since the time interval is not meaningful, T0 in block 241 is chosen such that (T0–T1)/X is greater than $R_T$ so that $T_P$ in the first iteration will always result in a "yes" determination of block 243.

If the block 243 determination is "yes", in block 245 temperature T and the actual, non-converted, fluid responses are stored in a temporary memory array, which is cleared each time the equipment is turned "on". In block 247 the method then determines if fluid temperature T is greater than or equal to a fixed temperature T3. Temperature T3 is selected such that fluid response data recorded in the temporary memory array between temperatures T1 and T3 allows a sufficiently accurate data-curve-fit over the temperature range from temperature T1 to the maximum temperature that the fluid may achieve in the equipment under any operating condition. If the block 247 determination is "yes" then in block 249 the data are curve-fit and new formulae or look-up tables substituted for the current formulae or look-up tables used to convert the fluid responses to constant temperature responses in block 163.

After the data are curve fit in block 249, or if the block 247 determination is "no", $T_P$ is set equal to T in block 251 and the method determines fluid quality and condition in blocks 169 to 227 the same as the embodiments in FIGS. 8 and 9. In each iteration of the embodiment of FIG. 10, the method continues to record the fluid temperature and responses in block 245, and, if the fluid temperature T is greater than T3, to curve-fit the data and update conversion formulae or look-up tables, until the rate of fluid temperature increase is determined in block 243 to be less than $R_T$. When the block 253 determination is "no", "A" is set equal to 1 before advancing to step 169. With A=1, the block 95 determination for all future iterations until the equipment is turned "off" is "no". Hence, fluid-response conversion formulae or look-up tables can only be updated once each time the equipment is turned "on", and can only occur if the initial rate of fluid temperature increase is greater than or equal to rate $R_T$ between the temperatures T1 and T3. Rate $R_T$ and temperatures T1 and T3 are selected such that: 1) the conversion formulae or look-up tables are updated on a sufficiently regular interval, especially when an essentially complete fluid change occurs in the equipment; and 2) the updated conversions are sufficiently accurate for determining fluid quality and condition over the fluid's operating temperature range in the equipment.

In this manner, the embodiment of FIG. 10 allows for changes in the temperature dependent variations of fluid responses $S_H$, $S_M$ and $S_L$ as the fluid ages during use and for changes of temperature dependencies when fluids of different formulation are added to the equipment.

While the embodiment of FIG. 10 uses low-, medium- and high frequency responses to determine fluid quality and conditions, a similar embodiment could be shown where the high-frequency response $S_H$ in not used in the determination for fluids in applications where the change in the fluid's high-frequency response is substantially less significant than the fluid's medium- and low-frequency response changes.

Figure 11:
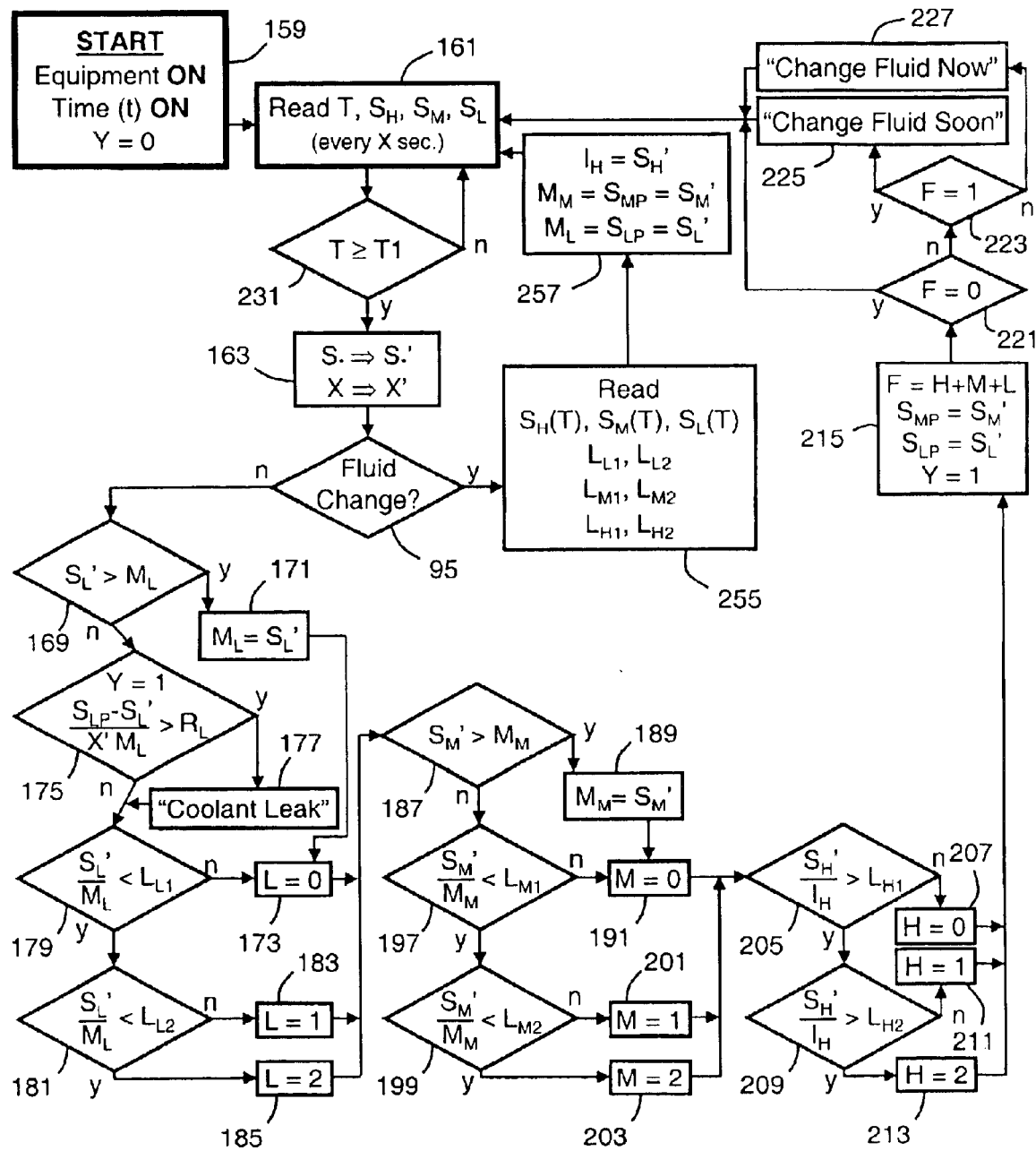
FIG. 11 is a flow chart of a feature of the present invention wherein the functions used to convert or correct fluid response data for fluid temperature variations and the thresholds used to determine fluid condition are updated when the fluid is changed.

FIG. 11 shows another embodiment of a feature of the present invention for determining the quality and condition of a fluid in equipment where in addition to converting fluid responses above a fixed first temperature threshold to eliminate or minimize effects of temperature variations, the formulae or look-up tables used for the data conversions can be updated each time a fluid change is made. Also the thresholds for determining the condition of the fluid can be updated each time a fluid change is made.

Referring to FIG. 11, as in the embodiment of FIG. 9, each time the equipment is turned "on", the variable "Y" is set equal to zero in block 159, and responses $S_H$, $S_M$, $S_L$ and temperature T are read in block 161. In block 231 the method determines if fluid temperature T is greater than or equal to a fixed temperature T1, and if the determination is "yes", the fluid responses $S_H$, $S_M$ and $S_L$ are converted to constant temperature fluid responses $S_H'$, $S_M'$, $S_L'$ and the time interval X between reading fluid responses is corrected to a constant temperature interval X'. In block 95 the method determines if fluid has been essentially completely changed since the last method iteration. As previously described, the determination of block 95 can be based on an input from a sensor or sensor system that detects fluid change by fluid level changes or other means, can be based on a subroutine that use $S_H$, $S_M$ and $S_L$, or $S_H'$, $S_M'$ and $S_L'$, or on an external input from a maintenance person or operator.

In this embodiment, however, the determination is typically based on an input from a maintenance person or operator, because if the determination of block 95 is "yes", the method in block 255 reads fluid response conversion formulae or look-up tables $S_H(T)$, $S_M(T)$, $S_L(T)$ and thresholds $L_{L1}$, $L_{L2}$, $L_{M1}$, $L_{M2}$, $L_{H1}$, $L_{H2}$, which, if different than the fluid used previously, can be input by a maintenance person or operator using a means for inputting, for example a keypad of a remote input, and in block 257 the method 167 initializes $I_H$, $M_M$, $S_{MP}$, $M_L$, and $S_{LP}$, and returns to block 161 where fluid responses and temperature are again read X seconds after the previous reading. If the block 95 determination is that the fluid has not been changed, than the method advances to blocks 169 to 227 where except for not having blocks 193, 195 the method is the same as the method embodiment described in FIG. 8. The determination of block 193 and the setting of the high-frequency thresholds, $L_{H1}$, $L_{H2}$, in block 195 of the method of FIG. 8 are not needed since the appropriate high temperature thresholds for the fluid are read in block 255 of the embodiment in FIG. 11.

In this manner the embodiment of FIG. 11 allows for changes in fluid temperature response and condition thresholds when a fluid of different formulation is added to the equipment.

While the embodiment of FIG. 11 does not determine the quality of the fluid as in blocks 193 and set the high-frequency thresholds, $L_{H1}$, $L_{H2}$, as in blocks 167, 195 of the embodiment in FIG. 8, an embodiment similar to that of FIG. 11 can read the high-frequency thresholds for a premium and a non-premium fluid, "Hi" and "Lo" respectively and have the high frequency thresholds set as in as in block 167, 193, 195 of FIG. 8.

While the embodiment of FIG. 11 reads fluid response conversion formulae or look-up tables $S_H(T)$, $S_M(T)$, $S_L(T)$ and thresholds $L_{L1}$, $L_{L2}$, $L_{M1}$, $L_{M2}$, $L_{H1}$, $L_{H2}$, when the fluid is essentially completely changed, other embodiments need not read all of these inputs and may also read other inputs, for examples rates $R_L$ and $R_L$ when the fluid is changed.

While the embodiment of FIG. 11 uses low-, medium- and high frequency responses to determine fluid condition, a similar embodiment could be shown where the high-frequency response $S_H$ in not used in the determination for fluids in applications where the change in the fluid's high-frequency response is substantially less significant than the fluid's medium- and low-frequency response changes.

In block 95 of the embodiments shown in FIGS. 6 to 11, a determination is made whether fluid has been essentially completely change since the last method iteration in order to determine when variables are reset, and, in the embodiment of FIG. 11, inputs are read. As previously described, that determination can be based on an external input, for examples an input from a maintenance person or operator, or from a sensor or sensor system that detects fluid change by fluid level changes or other means, or the determination can be based on a subroutine the uses that uses $S_H$, $S_M$ and $S_L$, or $S_H'$, $S_M'$ and $S_L'$. Shown in FIG. 12 is a flow chart of a subroutine that can be used in block 95 of FIGS. 6 and 7 that uses fluid data to determine if the fluid has been essentially completely changed since the last time the equipment was "on".

Figure 12:
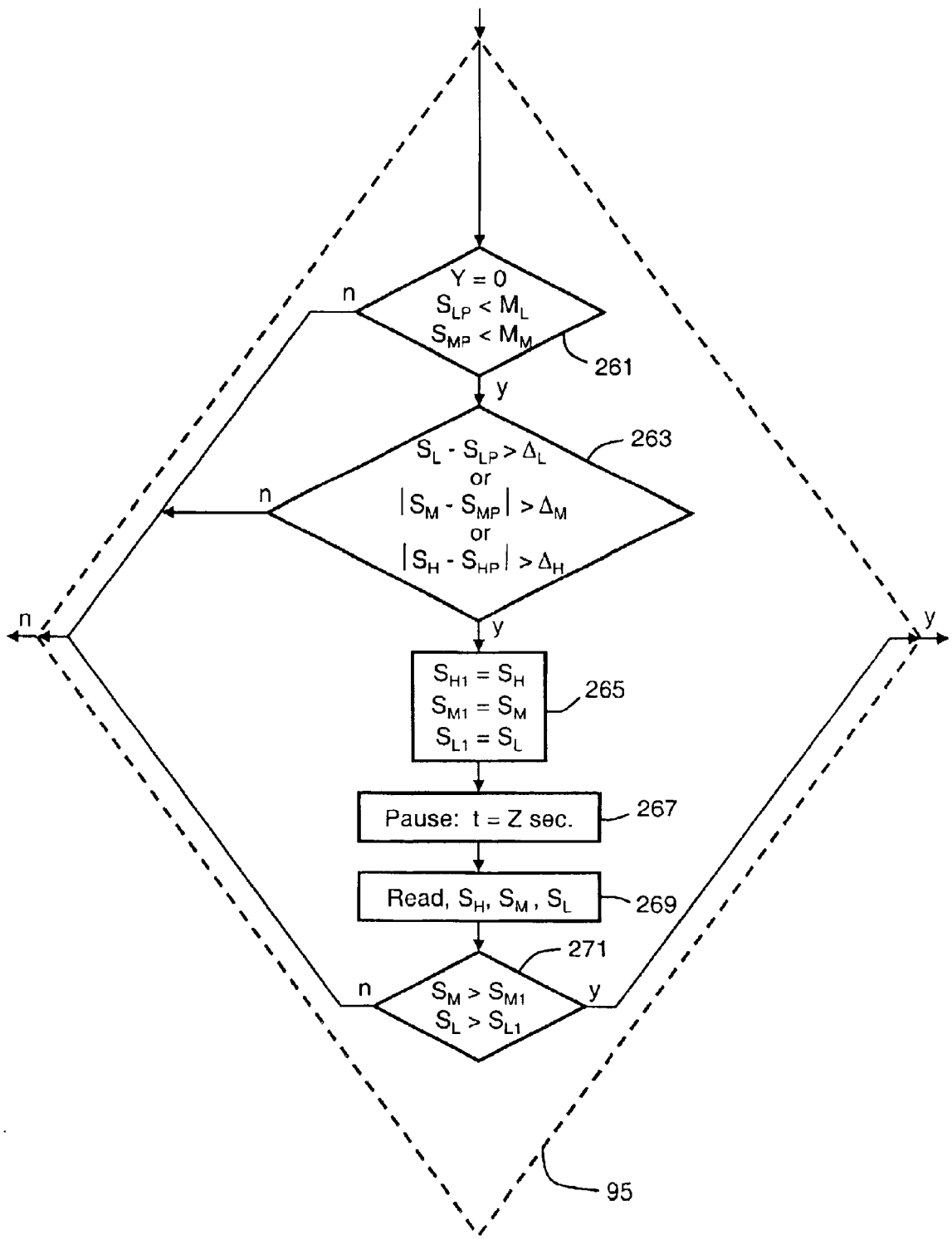
FIG. 12 is a flow chart of a feature of a subroutine for use in an embodiment of the present invention where the high-, medium- and low-frequency fluid response data are used to determine that the fluid has been essentially completely changed since the last time the equipment was "on".

Referring to FIG. 12, shown is a dashed outline of decision block 95 with input at the top and "yes" output on the right and "no" output on the left. Inputted into block 95 are the fluid responses $S_H$, $S_M$ and $S_L$ that were read in block 93 of FIG. 6 and the values for the other variables used by the method. In block 261 a determination is made if variable "Y" equals 0 and if the previous low- and medium-frequency fluid responses $S_{LP}$, $S_{MP}$ respectively, are less than their maximum response values $M_L$, $M_M$ respectively. This subroutine assumes that an essentially complete fluid change only occurs when the equipment is "off" and fluid change need only be detected on the first iteration of the method after the equipment is turned "on". Hence, if "Y" is not equal to zero, that is, if this is not the first iteration of the method after the equipment is turned "on", the determination of block 261 is "no" and the subroutine exits block 95 with a determination that "no" oil change has occurred. This subroutine also assumes that an essentially complete fluid change will not occur before low- and medium-frequency responses have reached their maximum value. Hence, if the previous responses, $S_{MP}$, $S_{LP}$ are not less than their respective maxima $M_M$, $M_L$, which were recorded the last method iteration before the equipment was last turned "off", then a fluid change did not occur, the determination of block 261 is "no" and the subroutine exits block 95 with a determination that "no" oil change has occurred. If the determination of block 261 is "yes" the subroutine in block 263 determines if there has been a major change in at least one of the fluid responses since the equipment was last turned "off". A major change in the low-frequency response is define as the response $S_L$ read the first iteration after the equipment is turned "on" minus the response $S_{LP}$, read the last iteration before the equipment was turned "off" being greater than a fixed value $\Delta_L$. A major change in the medium-frequency response is define as the absolute value of the response $S_M$ read the first iteration after the equipment is turned "on" minus the response $S_{MP}$ which was read the last iteration before the equipment was turned "off" being greater than a fixed value $\Delta_M$. Similarly, a major change in the high-frequency response is define as the absolute value of the response $S_M$ read the first iteration after the equipment is turned "on" minus the response $S_{MP}$ which was read the last iteration before the equipment turned "off" being greater than a fixed value $\Delta_M$. The reason that the absolute value is not taken of the low-frequency data is because a major decrease in low-frequency response, with no major change in the other fluid responses is more likely be a coolant leak than a fluid change. Hence, if the block 263 determination is "no", the subroutine exits block 95 with a "no" determination. If the block 263 determination is "yes", i.e. at least one of the fluid responses has a major change, the subroutine stores the current fluid responses $S_H$, $S_M$, $S_L$ in block 265 as $S_{H1}$, $S_{M1}$, $S_{L1}$ respectively, pauses a fixed time "Z" in block 267 before reading new fluid responses $S_H$, $S_M$ and $S_L$ in block 269. The subroutine then determines in block 271 if the new $S_M$, $S_L$ are greater than the stored previous values $S_{M1}$, $S_{L1}$ respectively. If the fluid has had an essentially complete change, the low- and medium-frequency responses will be increasing. Hence, a "no" determination in block 271 causes the subroutine to exit block 95 with a "no" determination, and a "yes" determination in block 271 means the low- and medium-frequency responses are increasing as would be expected with an essentially complete fluid change, and causes the subroutine to exit block 95 with a "yes" determination, indicating that an essentially complete fluid change has occurred since the last time the equipment was "on".

A similar subroutine could be used for block 95 in the embodiments in FIGS. 8–11 except that the subroutine would use constant temperature responses $S_H'$, $S_M'$, $S_L'$, in blocks 263, 265 and 271, and a block would be added between blocks 269 and 271 where the read fluid responses $S_H$, $S_M$, $S_L$ were converted to constant temperature results $S_H'$, $S_M'$, $S_L'$.

Also a similar subroutine could be used for block 95 in the embodiment of FIG. 7 where only medium- and low-frequency responses $S_M$, $S_L$ are use to determine fluid quality and condition. A subroutine for FIG. 7 would exclude the major change in the high frequency response condition in block 263, exclude storing $S_H$ as $S_{H1}$ in block 265 and would not read $S_H$ in block 269.

By using a subroutine that uses fluid responses to determine when an essentially complete fluid change occurs, the invention is less vulnerable to reset errors that may occur if a service technician or operator must provide an input to the method.

The method of the present invention allows for the determination of fluid quality and condition in an equipment where there are wide variations in the formulation of the fluid, which is shown in the following example.

EXAMPLE

An apparatus, which includes of a impedance/dielectric analyzer and a pair of parallel-disk electrodes each with surface area of about 3 cm$^2$ and separated by about 0.1 mm was used to determine the signal response of fluids of varying formulation tested in an industry standard Sequence IIIF test that rates oils for passenger car, gasoline engine application. In particular, the Sequence IIIF test is an about 85.5 hour oil test that uses a specially prepared Buick 3.8 L V-6 gasoline engine operated under determined conditions. During the test, oil samples are removed from the engine at about 10 hr intervals and at the end of the test, and the oil samples are tested using standard laboratory procedures for carbonyl and nitration increases (ASTM #839E), viscosity increase at about 40° C. (ASTM D2270), TBN (ASTM D4739) and TAN (ASTM D664A). These laboratory procedures are used to determine the operating condition of the oil, such that when one or more of the procedure results exceeds a limit, the oil has reached the end of its useful life in the engine. If any oil sample is found to be at the end of its useful life, that oil has failed the Sequence IIIF test.

For oils in the Sequence IIIF test, the dielectric/impedance analyzer sequentially applied about 3 V peak-to-peak electrical signals to the electrodes immersed in the oil at about 1 Hz with an about 3 V offset such that the signal oscillated from about +1.5 V to about +4.5 V relative to ground, and at about 100 Hz and about 1 MHz with about zero volt offset set such that the signals oscillate from about −1.5 to about +1.5 V relative to ground. The dielectric/impedance analyzer determined the test oil's imaginary impedance ($Z_{im}$) at about 1 Hz, the test oil's real impedance ($Z_{real}$) at about 100 Hz and the test oil's dielectric ($\in$) at about 1 MHz. Engine oil between the electrodes was maintained at about a constant 80° C. temperature. The method of this invention was used to determine when to signal "Change Fluid Soon" and "Change Fluid Now" with an determination embodiment similar to that shown in FIG. 6 except that, since all fluids were tested to meet the same quality standard, the high frequency thresholds were held fixed, eliminating the need for blocks 123 and 125 and the need for resetting the high frequency thresholds in block 97 when the fluid was changed in the engine for the next fluid test. For the tests, thresholds for the method were the following: $L_{L1}$=0.6, $L_{L2}$=0.2, $L_{M1}$=0.8, $L_{M2}$=0.5, $L_{H1}$=1.08, and $L_{H2}$=1.1. The rate for determining if there was a coolant leak, $R_L$, was 0.05/hr.

Four substantially different oil formulations were tested. One oil passed the engine test, the other three oils failed the engine test as determine by one or more of the standard laboratory procedures. No tests were failed due to a coolant leak. Shown in Table 1 are the engine test times when the method of this invention warned to "Change Fluid Soon" and to "Change Oil Now", and when and what laboratory procedure(s) determined the engine oil failed. The "Change Fluid Now" and "Change Fluid Now" times are rounded to the nearest hour. Since fluids are removed from the engine for the laboratory procedures at about 10 hour intervals, the laboratory determined "fail" is an upper limit with the failure having occurred sometime during the previous 10 hours. Table 1 demonstrates good correlation between the "Change Oil Now" warning and a failure determined by the laboratory procedures.

TABLE 1

| Fluid | "Change Oil Soon" | "Change Oil Now" | Laboratory Determined Failure |
|---|---|---|---|
| #1 | Pass | Pass | Pass |
| #2 | 24 hr | 53 hr | Carbonyl - 70 hr |
| #3 | 15 hr | 22 hr | TAN - 30 hr |
| #4 | 20 hr | 21 hr | Carbonyl & TAN - 30 hr |

While particular embodiments of the present invention have been shown and described, it is apparent that various combinations, changes and modification may be made therein to meet fluid analysis needs of various applications without departing from the invention in its broadest aspects. In particular, with regard to various functions performed by the above described invention, the terms (including any reference to a "means") used to describe individual components or sub-systems of the invention are intended to correspond, unless otherwise indicated, to any component or sub-system which performs the specified function of the described component or sub-system (e.g. that is functionally equivalent), even though not structurally or electronically equivalent to the described component or sub-system which performs the function in the herein illustrated embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method for determining the condition of a non-aqueous fluid comprising:
   (a) applying i) a low frequency, fixed amplitude, non-zero-offset voltage signal, ii) a medium frequency, fixed amplitude, zero-offset voltage signal, and iii) a high frequency, fixed amplitude, zero-offset voltage signal between electrodes immersed in the fluid,
   (b) measuring a fluid's response to the applied signals and determining i) a low-frequency fluid property, ii) a medium-frequency fluid property, and iii) a high-frequency fluid property,
   (c) comparing i) the magnitude and rate of change of the determined low-frequency fluid property, relative to the peak value of that low-frequency property for the fluid, to low-frequency thresholds, ii) the magnitude of the determined medium-frequency fluid property, relative to the peak value of that medium-frequency property for the fluid, to medium frequency thresholds, and iii) the magnitude of the determined high-frequency fluid response, relative to that high-frequency property when the fluid is fresh, to high-frequency thresholds, resulting in the determination of the fluid's quality and condition, wherein each step is conducted continuously, intermittently, repeatedly and combinations thereof and wherein the thresholds for comparing the determined fluid properties are selected from at least one of the group consisting of fixed, undated by external input and combinations thereof.

2. The method of claim 1 wherein the frequencies of the applied signals and offset voltage of the low-frequency applied signal is predetermined as a function of at least one of the following selected from the group consisting of electrode geometry, fluid temperature, fluid temperature range, composition of the fluid being monitored and combinations thereof.

3. The method of claim 1 wherein the low frequency is in the range of about 10 mHz to 10 Hz, the medium frequency is in the range of about 1 Hz to 500 kHz, the high frequency is in the range of about 10 kHz to 10 MHz, and the low frequency offset voltage is in the range of about 500 mV to 6.0 V.

4. The method of claim 1 wherein the fluid response to the applied signals is measured at fixed temperature with the temperature dependent upon the fluid employed.

5. The method of claim 1 wherein the fluid response to the applied signals is measured at variable temperatures in the range of ambient temperatures to maximum operating temperatures and the fluid properties determinations are selected from at least one of the group consisting of converting the properties to essentially fixed-temperature properties, minimizing the effect of temperature variation, using; a temperature dependent formulae, using a temperature dependent look-up tables and combinations thereof.

6. The method of claim 5 wherein the means for converting the fluid properties to essentially fixed-temperature fluid properties is selected from at least one of the group consisting of fixed, updated by external input, automatically updated when fluid temperature increases between two temperature thresholds at greater than a preset rate and combinations thereof.

7. The method of claim 1 wherein i) the determined low-frequency fluid property is selected from one of the group consisting of an imaginary-impedance, imaginary-impedance equivalent and combinations thereof; ii) the determined medium-frequency fluid property is one selected from the group consisting of: real-impedance, real-impedance equivalent and combinations thereof; and iii) the determined high-frequency fluid property in one selected from the group consisting of: dielectric, dielectric equivalent and combinations thereof.

8. The method of claim 1 wherein the high frequency thresholds are dependent upon a rate of change of the medium frequency response.

9. The method of claim 1 that further includes resetting the comparison values under the conditions selected from the group consisting of an external input is provided that a fluid change has occurred, change in the determined fluid properties are used to determine that a fluid change has occurred and combinations thereof.

10. A method for determining the condition of a non-aqueous fluid comprising:
- a) applying i) a low frequency, fixed amplitude, non-zero-offset voltage signal, and ii) a medium frequency, fixed amplitude, zero-offset voltage signal between electrodes immersed in the fluid,
- b) measuring a fluid response to the applied signals and determining i) a low-frequency fluid property, and ii) a medium-frequency fluid property,
- c) comparing i) the magnitude and rate of change of the determined low-frequency fluid property, relative to the peak value of that low-frequency property for the fluid, to low-frequency thresholds, and ii) the magnitude and rate of change of the determined medium-frequency fluid property, relative to the peak value of that medium-frequency property for the fluid, to medium frequency thresholds, resulting in the determination of the fluid's quality and condition, wherein i) the determined low-frequency fluid property is selected from one of the group consisting of imaginary-impedance, imaginary-impedance equivalent and combinations thereof, and ii) the determined medium-frequency fluid property is one selected from the group consisting of real-impedance, real-impedance equivalent and combinations thereof, wherein each step is conducted continuously, intermittently, repeatedly, and combinations thereof and wherein the thresholds for comparing the determined fluid properties are selected from at least one of the group consisting of fixed, undated by external input and combinations thereof.

11. The method of claim 10 wherein the frequencies of the applied signals and offset voltage of the low-frequency applied signal is predetermined as a function of at least one of the following selected from the group consisting of electrode geometry, fluid temperature, fluid temperature range, composition of the fluid being monitored and combinations thereof.

12. The method of claim 10 wherein the low frequency is in the range of about 10 mHz to 10 Hz, the medium frequency is in the range of about 1 Hz to 500 kHz, and the low frequency offset voltage is in the range of about 500 mV to 6.0 V.

13. The method of claim 10 wherein the fluid response to the applied signals is measured at variable temperatures in the range of ambient temperatures to maximum operating temperatures and the fluid properties determinations are selected from at least one of the group consisting of converting the properties to essentially fixed-temperature properties, minimizing the effect of temperature variation, using; a temperature dependent formulae, using a temperature dependent look-up tables and combinations thereof.

14. The method of claim 13 wherein the means for converting the fluid properties to essentially fixed-temperature fluid properties is selected from at least one of the group consisting of fixed, able to be updated by external input, automatically updated when fluid temperature increases between two temperature thresholds at greater than a preset rate and combinations thereof.

15. The method of claim 10 that further includes resetting the comparison values under the conditions selected from the group consisting of: an external input is provided that a fluid change has occurred, change in the determined fluid properties are used to determine that fluid change has occurred and combinations thereof.

16. The method of claim 10 wherein the fluid response to the applied signals is measured at fixed temperature with the temperature dependent upon the fluid employed.

* * * * *